(12) United States Patent
Kim et al.

(10) Patent No.: US 11,359,245 B2
(45) Date of Patent: Jun. 14, 2022

(54) METHOD FOR DETERMINING DECREASE IN FUNCTIONS OF HIPPOCAMPUS BY USING CORRELATION BETWEEN MICRO RNA AND NMDA RECEPTOR, METHOD FOR INHIBITING DECREASE IN FUNCTIONS, AND METHOD FOR SCREENING FOR INHIBITORS OF DECREASE IN FUNCTIONS

(71) Applicants: DAEGU GYEONGBUK INSTITUTE OF SCIENCE AND TECHNOLOGY, Daegu (KR); INSTITUTE FOR BASIC SCIENCE, Daejeon (KR)

(72) Inventors: Keetae Kim, Daegu (KR); Hong Gil Nam, Daegu (KR); Chand Parvez Danka Mohammed, Daegu (KR)

(73) Assignees: DAEGU GYEONGBUK INSTITUTE OF SCIENCE AND TECHNOLOGY, Daegu (KR); INSTITUTE FOR BASIC SCIENCE, Daejeon (KR)

( * ) Notice: Subject to any disclaimer, the term of this patent is extended or adjusted under 35 U.S.C. 154(b) by 0 days.

(21) Appl. No.: 16/889,372

(22) Filed: Jun. 1, 2020

(65) Prior Publication Data
US 2020/0318193 A1 Oct. 8, 2020

Related U.S. Application Data

(62) Division of application No. 15/736,949, filed as application No. PCT/KR2016/006465 on Jun. 17, 2016, now Pat. No. 10,704,099.

(30) Foreign Application Priority Data

Jun. 18, 2015 (KR) .......................... 10-2015-0086823

(51) Int. Cl.
| C12Q 1/6883 | (2018.01) |
| C12N 15/113 | (2010.01) |
| G01N 33/50 | (2006.01) |
| G01N 33/68 | (2006.01) |

(52) U.S. Cl.
CPC .......... *C12Q 1/6883* (2013.01); *C12N 15/113* (2013.01); *G01N 33/5023* (2013.01); *G01N 33/5058* (2013.01); *G01N 33/6893* (2013.01); *C12N 2310/11* (2013.01); *C12N 2310/113* (2013.01); *C12N 2310/141* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 10,087,443 B2 * 10/2018 Schaefer .............. A61K 38/185

OTHER PUBLICATIONS

Kaalund et al. Epilepsia 55: 2017-2024 (Year: 2014).*
Hu et al. Cell Death and Disease 8, e2717, pp. 1-9 (Year: 2017).*

* cited by examiner

*Primary Examiner* — Brian Whiteman
(74) *Attorney, Agent, or Firm* — Lex IP Meister, PLLC

(57) ABSTRACT

The present invention relates to a method for determining a decrease in the functions of the hippocampus by using the correlation between a micro RNA (miRNA) and an N-methyl-D-aspartate receptor (NMDAR), a method for inhibiting the decrease in the functions, and a method for screening for inhibitors of the decrease in the functions. The present invention confirms that miR-204, among miRNAs up-regulated in an aged hippocampus, decreases the expression of EphB2, by accurately targeting EphB2, which is an important regulatory receptor, resulting in a decrease in the neuronal surface expression of an NR1 subunit of an NMDAR in hippocampal nerves and a decrease in the density of dendrites, thereby having an effect of determining whether the functions of the hippocampus are decreased, by using the correlation between a miRNA and an NMDAR, and furthermore, has an effect of providing a method for inhibiting the decrease in the functions of the hippocampus, and a method for screening for inhibitors of the decrease in the functions.

3 Claims, 15 Drawing Sheets

Specification includes a Sequence Listing.

METHOD FOR DETERMINING DECREASE IN FUNCTIONS OF HIPPOCAMPUS BY USING CORRELATION BETWEEN MICRO RNA AND NMDA RECEPTOR, METHOD FOR INHIBITING DECREASE IN FUNCTIONS, AND METHOD FOR SCREENING FOR INHIBITORS OF DECREASE IN FUNCTIONS

CROSS-REFERENCE TO RELATED APPLICATION

This application is a Divisional Application of U.S. patent application Ser. No. 15/736,949 filed on Dec. 15, 2017, which is a National Stage application of PCT/KR2016/006465 filed on 17 Jun. 2016, which claims which claims priority to and the benefit of Korean Patent Application No. 10-2015-0086823 filed on Jun. 18, 2015, the disclosure of which is incorporated herein by reference in its entirety.

BACKGROUND

1. Field of the Invention

The present disclosure relates to a method for determining decrease in functions of hippocampus using correlation between micro RNA (mRNA) and N-methyl-D-aspartate receptor (NMDA receptor; NMDAR), a method for inhibiting decrease in functions, and a method for screening for inhibitors of decrease in functions, more particular, since as the expression of miRNA-204 increases in the aged hippocampus, the Eph/ephrin mediated axon guidance signaling pathway is down-regulated, which causes the expression of the hippocampal NMDA receptor is decreased, the present disclosure relates to determine that whether hippocampal function is decreased by using the correlation thereof, furthermore, to provide a method for inhibiting decrease in functions of the hippocampus and a method for inhibitors of decrease in functions.

2. Discussion of Related Art

The hippocampus is a key component of the brain system and is part of the cerebral cortex that protrudes from the floor of lateral ventricle inferior horn in the cerebrum. The hippocampus regulates learning, memory and awareness of new things, emotions, actions and some movements, and regulates the functions of the hypothalamus. The hippocampus above is undergoing biological and structural changes with age and affect age-related cognitive decline (C. A. Erickson and C. A. Barnes, *Experimental Gerontology*, 38:61, 2003). Neurocontrol defects caused by aging can affect the memory and learning abilities of the aged hippocampus, which can lead to Alzheimer's dementia, epilepsy, and Clover-Verse syndrome (Ryann M. Fame et al., *Trends Neurosci.* 34(1):41, 2011; Federico W. Grillo et al., *PNAS*, 110(16):E1514, 2013).

In particular, the brain is formed by a network of neuron (nerve cell) connected by synapses, and our memory information is generated in such a way that the synapses, the connection structure between neurons, are changed. When a gene related to memory is expressed and a protein is made, memory contents are preserved and maintained for a long time, and synaptic plasticity changes in aging process. The synaptic plasticity implies a structural or biochemical change in synapses that changes the effect of post-synaptic neurons, and electrical stimulation of circuits in the hippocampus can induce long-term synaptic changes that appear to be associated with learning. N-methyl-D-aspartate receptor (NMDA receptor), a neuro-receptor known to regulate signaling of between cell death and normal cell, are found in the hippocampus, especially in the CA1 region, the NMDA receptor is known to regulate calcium throughout the body and to participate in long-term enhancement.

In addition, since the NMDA receptors interact directly with the dopamine D1 receptor and regulate cell death according to the result of the interaction or induce normal cell-to-cell communication, various studies have been conducted on NMDA receptors to treat various diseases such as stroke, schizophrenia, osteoporosis, epilepsy, and dementia. For example, It is a well-established academic theory that the blackout phenomenon, a phenomenon in which alcohol cannot be remembered after drinking alcohol, also occurs because alcohol acts on the brain to interrupt the activity of NMDA receptors. In other words, the above is because when NMDA activity is interrupted, the glutamate salt activity, which acts as a mediator between neurons in the brain, is stopped.

On the other hand, microRNA (miRNA) is a new material that binds to 3'-UTR of mRNA as a single-stranded RNA molecule of 21-25 nucleotides (nt) and regulates expression in eukaryotes. The production of the miRNA is made into a pre-miRNA of stemloop structure by Drosha (RNase III type enzyme), the pre-miRNA is made into miRNA by being transported to the cytoplasm and cleaved by Dicer. The miRNA is involved in development, cell proliferation and death, fat metabolism, tumor formation, and the like by regulating the expression of target proteins. The miRNAs having the function above have recently attracted attention as other epigenetic regulators other than histone deacetylases (HDACs) or DNA methyl transferases (DNMTs) (Miranda K C et al., *Cell*, 126(6):1203, 2006; Nicole Noren Hooten et al., *PLoS ONE*, 5(5):e10724, 2010).

It is well-known that about 50% of all mammalian miRNAs are abundant in the brain and many of the miRNAs have an important role in nerve and neural development (Sempere, L. F. et al., *Genome Biol.*, 5:R13, 2004; Giraldez, A. J. et al., *Science*, 308:833, 2005).

In the prior art, although it is reported as miRNAs in the entire brain of rat are potentially involved in the regulation of the aging process through the insulin signaling pathway (Sachi Inukai et al., *PLoS ONE*, 7(7):e40028, 2012), and it is known as regulation of neural activity is performed by interaction of downstream targets in the hippocampal miRNAs and the particular biological pathway (Stephen M. Eacker et al., *PLoS ONE*, 6(10):e25068, 2011), there is still a lack of comprehensive research on the effect of miRNA dynamic expression on normal hippocampal function in an aging-dependent manner.

Accordingly, the present inventors have made extensive efforts to study the role of miRNA in the normal aging process of the hippocampus, it was confirmed that of the miRNAs up-regulated in the aging hippocampus, miR-204 accurately targets EphB2 an important regulatory receptor and reduces EphB2 expression, and which causes neuronal surface expression of the NR1 subunit of the NMDA receptors in hippocampal nerves was decreased and dendritic density decreased was resulted in.

In addition, the present inventors determined that whether hippocampal function was decreased by using the correlation between microRNA and NMDA receptor, furthermore, confirmed that a method for inhibiting decrease in functions of the hippocampus and a method for screening inhibitors of decrease in functions can be provided, thus completed the present disclosure.

SUMMARY OF THE INVENTION

An object of the present disclosure is to provide a method for determining decrease in functions of hippocampus using correlation between micro RNA (mRNA) and N-methyl-D-aspartate receptor (NMDA receptor; NMDAR).

Another object of the present disclosure is to provide a method for inhibiting decrease in functions of hippocampus using correlation between miRNA and NMDA receptor.

Another object of the present disclosure is to provide an use for using of an agent which inhibits expression of miR-204-5p or inhibits an activity of miR-204-5p for preventing or treating decrease in functions of hippocampus.

Another object of the present disclosure is to provide a method for preventing decrease in functions of hippocampus, comprising: administering an agent which inhibits expression of miR-204-5p or inhibits an activity of miR-204-5p to an individual in need thereof in a pharmaceutically effective amount.

Another object of the present disclosure is to provide a method for treating decrease in functions of hippocampus, comprising: administering an agent which inhibits expression of miR-204-5p or inhibits an activity of miR-204-5p to an individual in need thereof in a pharmaceutically effective amount.

Another object of the present disclosure is to provide a method for screening for inhibitors of decrease in functions of hippocampus using correlation between miRNA and NMDA receptor.

The present disclosure, to achieve the first object, provides a method for determining decrease in functions of hippocampus, which includes: (a) analyzing an expression of a miR-204-5p represented by a base sequence of SEQ ID NO: 1 in a gene sample collected from a patient; and (b) determining whether the expression of the miR-204-5p from the patient is increased by using a gene sample collected from a normal person as a control group; according to increasing the expression of the miR-204-5p, further determining whether an expression of N-methyl-D-aspartate receptor (NMDA receptor; NMDAR) on a surface of a hippocampal nerves is decreased.

According to a preferred embodiment of the present disclosure, as the expression of the miR-204-5p is increased, an expression of an EphB2 protein may be decreased, and resulting in a decrease in an expression of a NMDA receptor in the hippocampal nerves.

According to a preferred embodiment of the present disclosure, as the expression of miR-204-5p is increased, an expression of a NR1 subunit may be decreased.

According to a preferred embodiment of the present disclosure, as the expression of the miR-204-5p gene is increased, a dendritic spine density of the hippocampal nerve may be decreased.

The present disclosure, to achieve the second object, provides a method for inhibiting decrease in functions of hippocampus, which includes: increasing an expression of a NMDA receptor by treating an agent that inhibits an expression of a miR-204-5p or inhibits an activity of a miR-204-5p.

According to a preferred embodiment of the present disclosure, the agent which inhibits the expression of the miR-204-5p or inhibits the activity of the miR-204—may be an antisense oligonucleotide or a siRNA.

According to a preferred embodiment of the present disclosure, the agent may be at least one selected from the group consisting of an antisense RNA 5'AGGCAUAG-GAUGACAAAGGGAA 3' (SEQ ID NO: 4).

According to a preferred embodiment of the present disclosure, as an expression of an EphB2 protein may be increased by the agent which inhibits the expression of the miR-204-5p or inhibits the activity of the miR-204-5p and resulting in a decrease in an expression of a NMDA receptor in a hippocampal nerves.

According to a preferred embodiment of the present disclosure, of the NMDA receptors, NR1 subunit expression may be increased.

According to a preferred embodiment of the present disclosure, a dendritic spine density of the hippocampal nerves may be increased by the agent that inhibits expression of miR-204-5p or inhibits an activity of a miR-204-5p.

The present disclosure, to achieve the third object, provides a method for screening an inhibitor of decrease in functions of hippocampus, which include: (a) treating a candidate which inhibits a miR-204-5p expression or inhibits an activity of a miR-204-5p in a human-derived hippocampal nerve; and (b) determining whether an expression of a NMDA receptor is increased on a surface of the nerve.

According to a preferred embodiment of the present disclosure, in the step (b), the candidate which increases the expression of the NMDA receptor may be selected.

According to a preferred embodiment of the present disclosure, in the step (b), further determining whether an expression of EphB2 protein increases, and the candidate which increases the expression of the EphB2 protein and the expression of the NMDA receptor may be selected.

According to a preferred embodiment of the present disclosure, in the step (b), whether the expression increased of the NR1 subunit in the NMDA receptor may be determined.

Further, the present disclosure may provide to a pharmaceutical composition for preventing or treating decrease in functions of hippocampus, comprising: an agent which inhibits expression of a miR-204-5p or inhibits an activity of a miR-204-5p, wherein the miR-204-5p is represented by the base sequence of SEQ ID NO: 1.

In addition, the present disclosure may provide to an use of an agent which inhibits an expression of miR-204-5p or inhibits an activity of miR-204-5p for preventing or treating decrease in functions of hippocampus, wherein the miR-204-5p is represented by a base sequence of SEQ ID NO: 1.

In addition, the present disclosure may provide to a method for preventing decrease in functions of hippocampus, which includes: administering an agent which inhibits an expression of a miR-204-5p or inhibits an activity of a miR-204-5p to an individual in need thereof in a pharmaceutically effective amount, wherein the miR-204-5p is represented by a base sequence of SEQ ID NO: 1.

Further, the present disclosure may provide to a method for treating decrease in functions of hippocampus, which includes: administering an agent which inhibits an expression of a miR-204-5p or inhibits an activity of a miR-204-5p to an individual in need thereof in a pharmaceutically effective amount, wherein the miR-204-5p is represented by a base sequence of SEQ ID NO: 1.

In the present disclosure, since it was confirmed that of the miRNAs up-regulated in the aging hippocampus, miR-204 accurately targets EphB2 an important regulatory receptor and reduces EphB2 expression, and which causes neuronal surface expression of the NR1 subunit of the NMDA receptors in hippocampal nerves was decreased and dendritic density decreased was resulted in, there are effects of determining whether hippocampal function was decreased by using the correlation between microRNA and NMDA receptor, furthermore, providing a method for inhibiting decrease in functions of the hippocampus and a method for screening inhibitors of decrease in functions.

DETAILED DESCRIPTION OF EXEMPLARY EMBODIMENTS

Figure 1A:
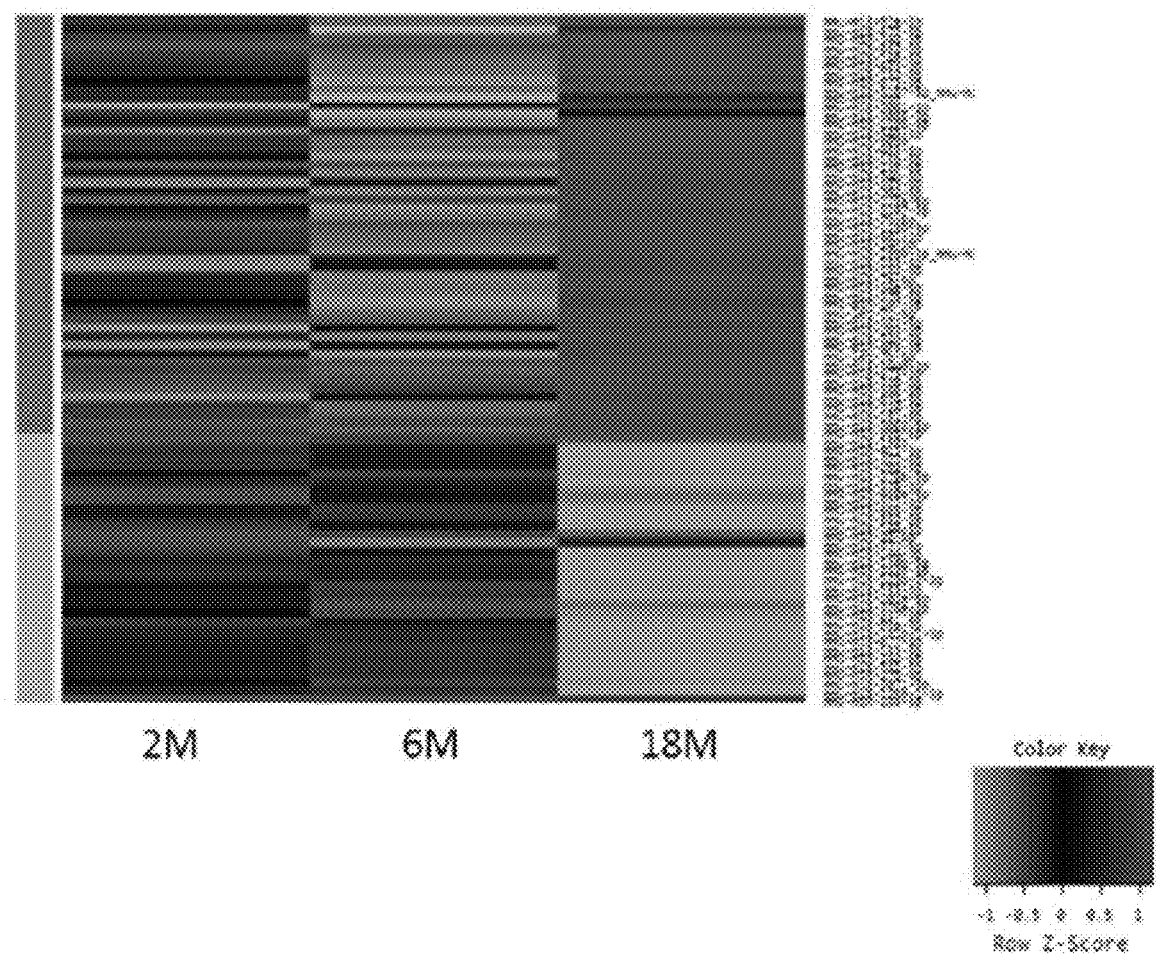
FIG. 1a illustrates an aging-dependent expression pattern of hippocampal mRNA, and illustrates a heat map of expression change of miRNA in hippocampus of 2 months, 6 months, and 18 months rats, miRNA with a fold change value of greater than 2.0 is about 80.

Hereinafter, the present invention is described in more detail.

As described above, although micro RNA (miRNA, hereinafter referred to as miRNA) in brain are known to play important roles in nerve and neural development, there is a lack of research on how the miRNA affects normal hippocampal function in an aging-dependent manner, depending on a regulation of miRNA expression.

The present disclosure, sought to solve the above-mentioned problems by providing a method for determining decrease in functions of hippocampus using correlation between micro RNA and NMDA receptor, a method for inhibiting decrease in functions, and a method for screening inhibitors of decrease in functions. Through the above, it was confirmed that of the miRNAs up-regulated in aged hippocampus, miR-204 reduces EphB2 expression by correctly targeting EphB2 which is an important regulatory receptor, which causes the expression of NR1 subunit of the NMDA receptor was decreased on the surface of the hippocampal nerve cell and dendritic density decrease was resulted in.

Accordingly, the present disclosure relates to a method for determining decrease in functions of hippocampus, comprises, (a) analyzing an expression of a miR-204-5p represented by a base sequence of SEQ ID NO: 1 in a gene sample collected from the patient;

(b) determining whether the expression of the miR-204-5p from the patient is increased by using a gene sample collected from a normal person as a control group;

according to increasing the expression of the miR-204-5p, further determining whether an expression of N-methyl-D-aspartate receptor (NMDA receptor; NMDAR) on a surface of a hippocampal nerves is decreased.

In addition, the present disclosure can provide a method for diagnosing memory impairment and a method for cognitive function inhibition using the method for determining decrease in functions of the hippocampus, further can provide a method for diagnosing dementia.

In the present disclosure, it is characterized that when the expression of EphB2 protein is decreased as the expression of the miR-204-5p is increased, the Eph/ephrin mediated axon guidance signaling pathway is down-regulated, which causes the expression of NMDA receptor in the hippocampal nerves is decreased, and preferably, it is characterized that of NMDA receptor on the cell surface of neuron (nerve cell), the expression of the NR1 subunit decreases.

In addition, it is characterized that as the expression of miR-204-5p gene is increased, the dendritic spine density in the hippocampal nerves is decreased.

The miR-204-5p expressed by the base sequence of SEQ ID NO: 1 (5'-uucccuuugucauccuaugccu-3') was known to inhibit the growth of cancer cells mainly (Binbin Zhang et al., *Medical Oncology*, 32(1):1, 2014), however, it was first confirmed by the present inventors that miR-204 reduces EphB2 expression by correctly targeting EphB2, which causes expression of the NR1 subunit of the NMDA receptor expressed on the surface in the hippocampal nerves is decreased cell and dendritic density decrease was resulted in.

The miR-204 or miR-204-5p nucleic acid molecule of the present disclosure can be originated from an animal including a human, for example, monkeys, pigs, horses, cows, sheep, dogs, cats, mice, rabbits, and the like, but it is not limited thereto. In addition, the miR-204 or the miR-204-5p nucleic acid molecule of the present disclosure can exist in a single-stranded or double-stranded form. Although mature miRNA molecule exists predominantly single-stranded, precursor miRNA (pre-miRNA) molecule exists predominantly self-complementary (for example, stem- and loop-structure) structure capable of forming double-stranded portion.

The nucleic acid molecule of the present disclosure can obtain information through a known sequence information database, for example, GenBank of NCBI, through above, may be separated or prepared by using standard molecular biology techniques, for example, chemical synthesis methods or recombinant methods, or commercially available ones can be used.

In one embodiment of the present disclosure, to understand the miRNA mediating a regulation of a hippocampal aging process, small RNA (small RNA; smRNA or sRNA, hereinafter referred to as sRNA) profiling was performed in male rats at 2 months, 6 months and 18 months. The sRNA is an RNA consisting of approximately 200 bases or less, which corresponds to eukaryotic cells and is known to exclude tRNA and ribosomal RNA.

As shown in FIG. 1a, a heat map analysis was performed to confirm miRNAs that were differentially expressed as the aging progressed, and of the total 269 miRNAs in the hippocampus, 80 miRNAs were confirmed to have fold change values greater than 2.0 for any two of the three different time periods. miRNAs showed significant increase in expression or decrease in expression, especially, The presence of miRNAs with significantly increased expression in a mouse of 18 months was confirmed.

Figure 1B:
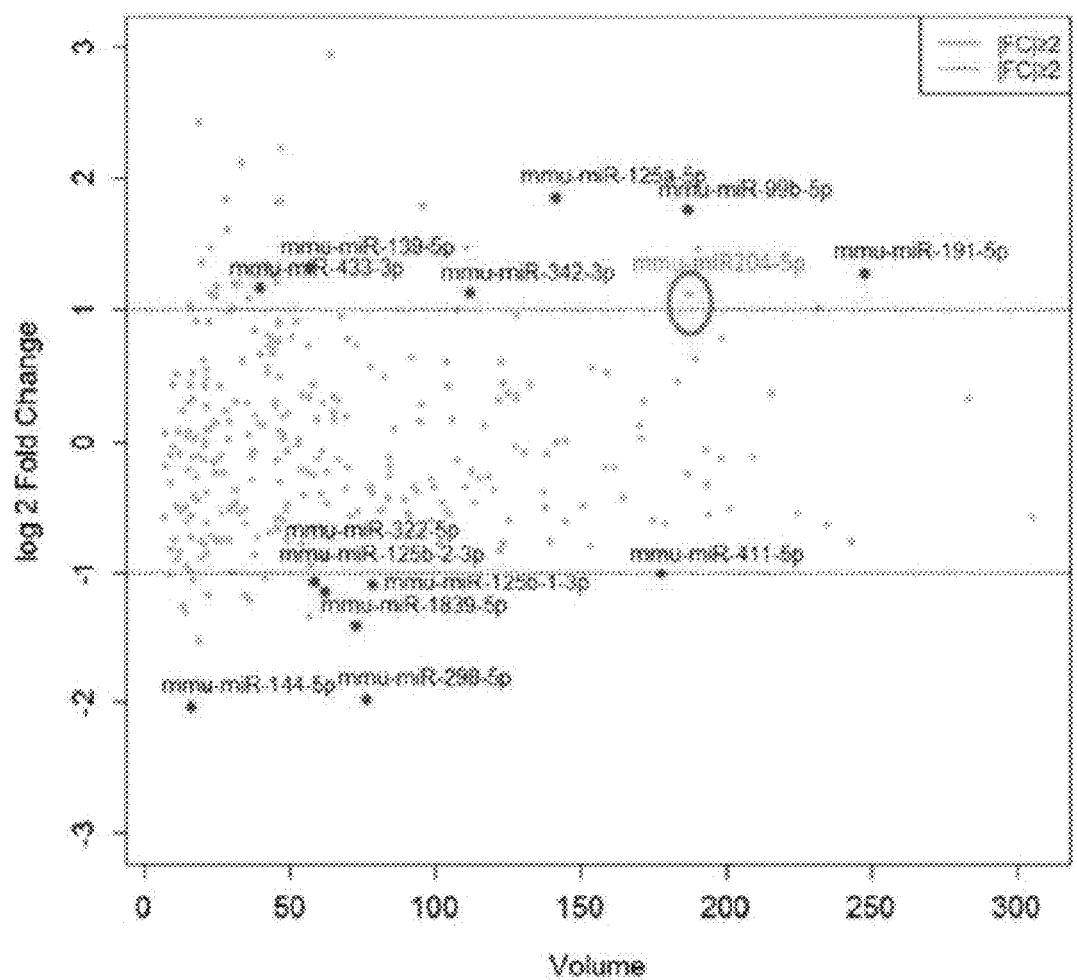
FIG. 1b illustrates a scattered volume plot of miRNA having a fold change value of greater than 2.0 between 2 months and 18 months rats, Representative miRNAs selected through qPCR assays are represented in red. The X axis represents a volume change and the Y axis represents an miRNA expression as the log the fold change value.
Figure 1C:
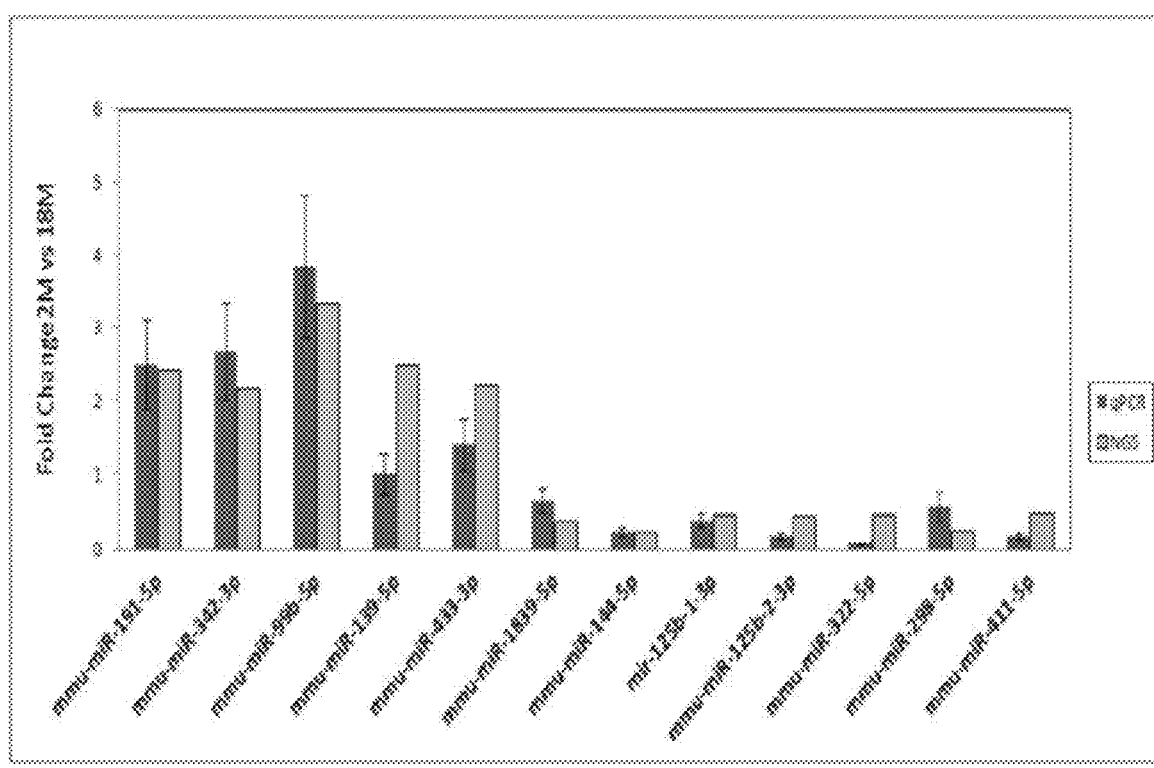
FIG. 1c illustrates a graph of data which represents the types of miRNAs having a fold change value of greater than 2.0 between 2 months and 18 months rats when analysis is performed using Real-Time Quantitative Polymerase Chain Reaction (qPCR).

As shown in FIG. 1b, in the sporadic volume configuration of 269 miRNAs expressed in the hippocampus during normal aging (between 2 months and 18 months), it was confirmed that 19 miRNAs were decreased more than 2-fold in expression, on the other hand, 36 miRNAs were increased more than 2-fold in expression. Also, to confirm the significance of sRNA data, twelve miRNAs having fold change values of 2.0 or greater in rats of 2 and 18 months were randomly selected (increase in expression: 5, decrease in expression: 7) and analyzed by real-time quantitative polymerase chain reaction (real-time quantitative PCR; qPCR). As shown in FIG. 1c, it was confirmed that the result were consistent with sRNA profiling data and sRNA profiling can reflect the entire miRNA expression pattern in hippocampal tissue.

Figure 2A:
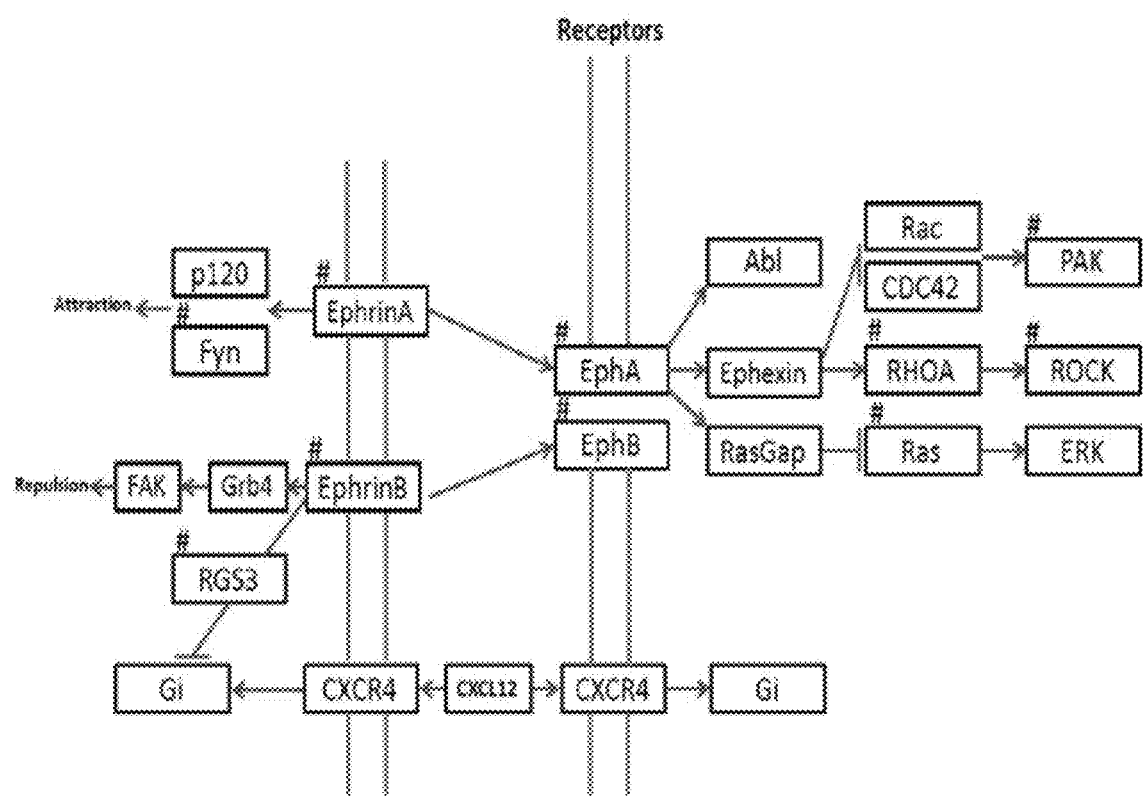
FIG. 2a illustrates modeled data a predicted pathway of Eph/ephrin mediated axon induction in hippocampal aging, and qPCR-verified targets are represented with #.

In the present disclosure, the expected target gene pathway of miRNAs was derived to determine the biological effects caused by miRNA expression regulation in hippocampal aging. As shown in Table 2, various biological effects were derived, although the cancer-related pathway was expected to be significantly significant, the follow-up study was carried out with a focus on the axon guidance pathway (P=4.5E-18), which has relatively little research in the aspect of aging. As the schematic diagram of the axon guidance pathway illustrated in FIG. 2a, in the present disclosure, the relationship between the activity of Eph/ephrin and miRNA was examined.

Figure 2B:
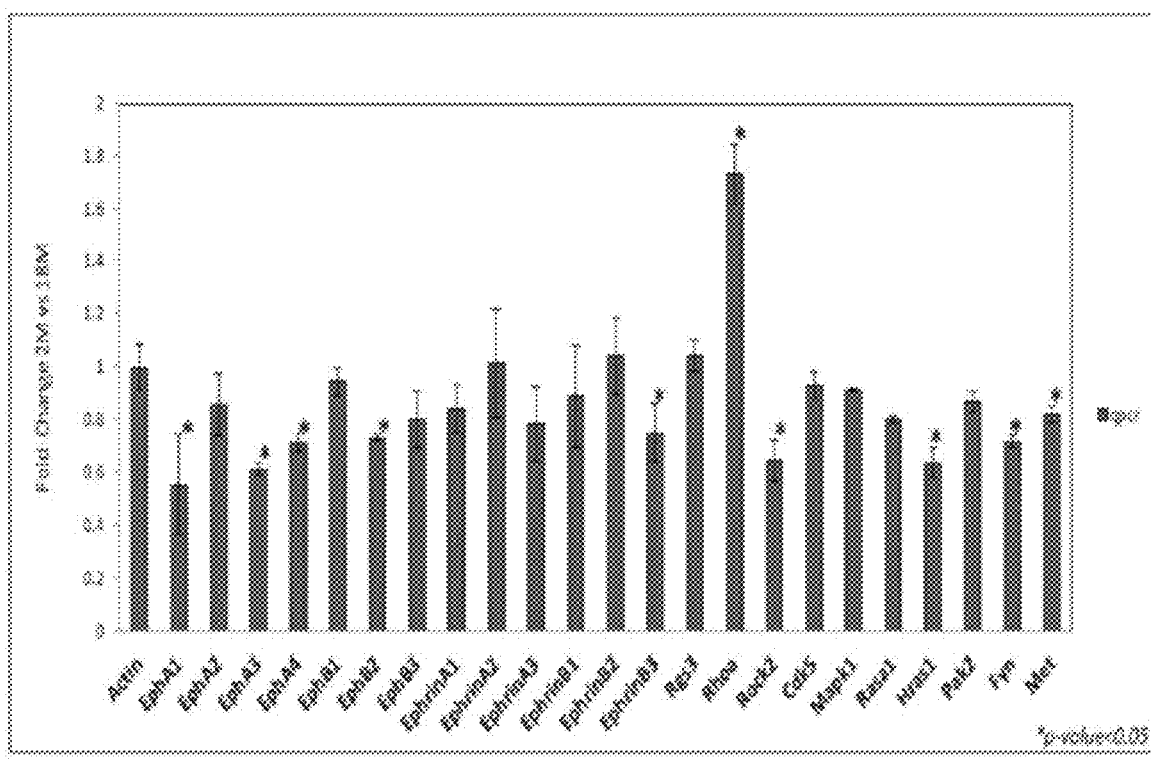
FIG. 2b illustrates data of a fold change value of a representative target mRNA included in the axon induction path using qPCR.

As shown in FIG. 2b, it was confirmed in the present disclosure that of the target molecules in the Eph/ephrin subfamily, the expression of 9 molecules were decreased in the aging process, no significant change was observed in 13 molecules, the expression of was homolog gene family (RhoA, member A) was only increased, using qPCR. This above shows down-regulation of Eph/ephrin mediated axon induction pathway by aging, on the whole. In particular, EphA1 and EphB2, two ephrin receptors known to regulate synaptic plasticity, were found to be approximately 30% and 25% decreased in mRNA expression, respectively.

Figure 2C:
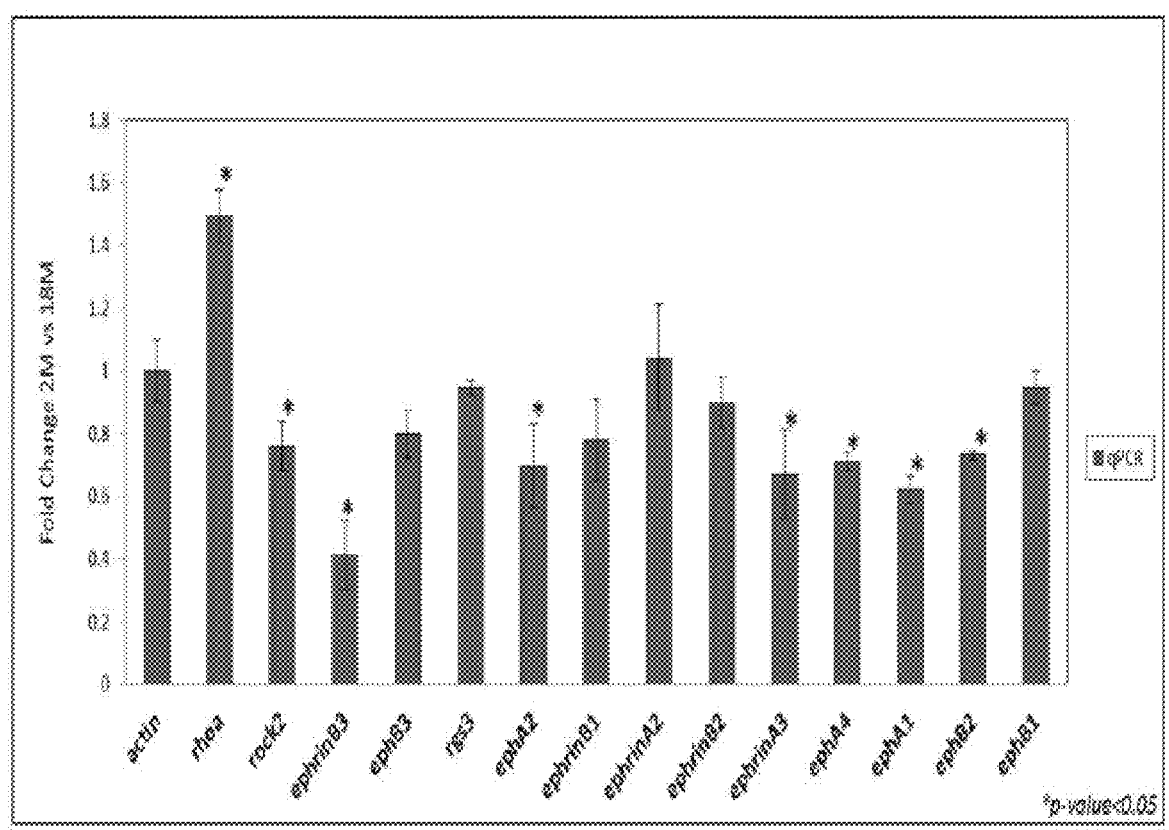
FIG. 2c illustrates data of a fold change value of target mRNA involved in Eph/ephrin signal in hippocampal tissue using qPCR.

To confirm down-regulation of ephrin signal pathway by aging, as shown in FIG. 2c, the fold change values of the target mRNAs involved in the Eph/ephrin signal in hippocampal tissues of 2 and 18 months rats were analyzed using qPCR. The results of the analysis generally corresponded to the sRNA profile analysis results of the present disclosure, it was confirmed that EphrinB3, which was a single ephrin subunit, and EphA1, EphA2, EphA4 and EphB2, which were four ephrin receptor subunits, were decreased mRNA expression by 25 to 60%, on the other hand, RhoA mRNA was increased expression by 50%.

Figure 2D:
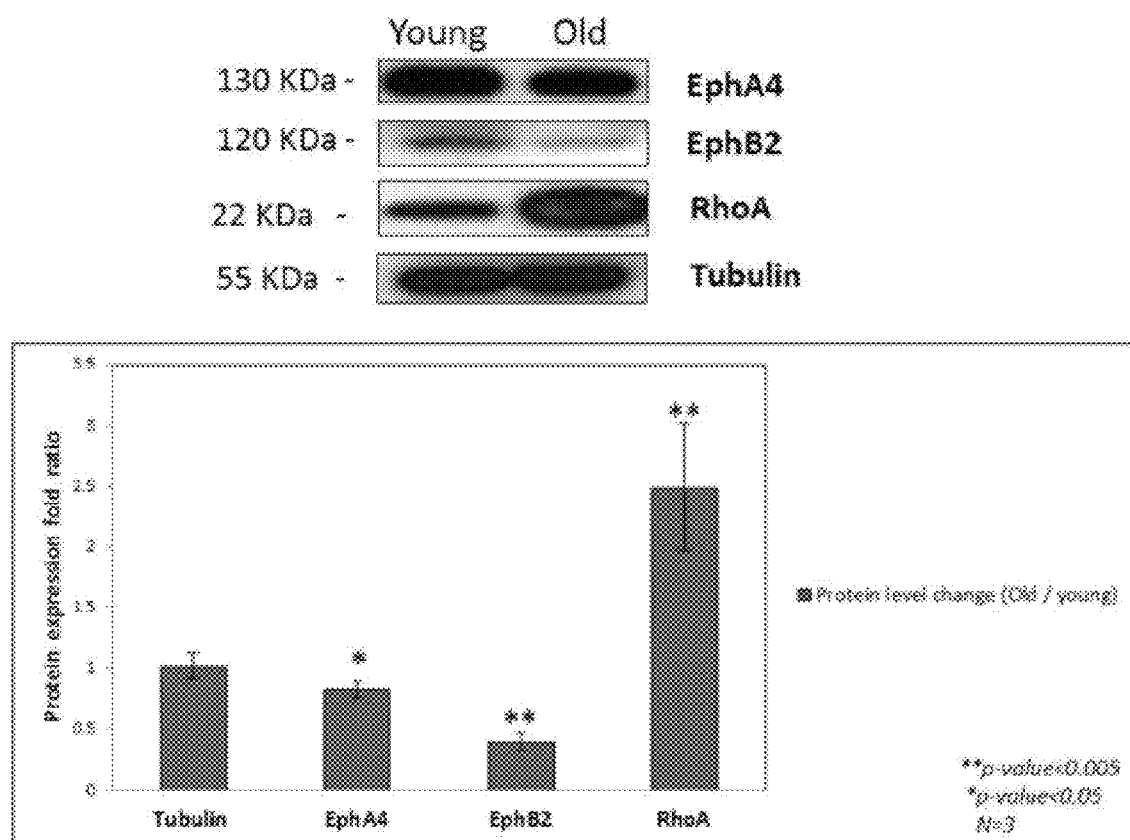
FIG. 2d illustrates data of protein expression of target molecules involved in ephrin signaling in young hippocampal tissue and old hippocampal tissue determined by Western blot analysis.

In addition, to confirm whether the protein expression of the above molecules also changed with aging, the degree of protein expression for RhoA, EphA4 and EphB2 was confirmed, as a result, as shown in FIG. 2d, it was confirmed that EphA4 and EphB2 was decreased protein expression by 60% and 30%, respectively, RhoA was increased protein expression up to 150%.

In the present disclosure, EphB2 which is one of the positive regulators that regulate synaptic plasticity in the ephrin signal pathway, is important for neuroplasticity and is known to cause cognitive dysfunction in Alzheimer's disease, was selected as a target of miRNA which expression is significantly regulated in the aging period.

Figure 3:
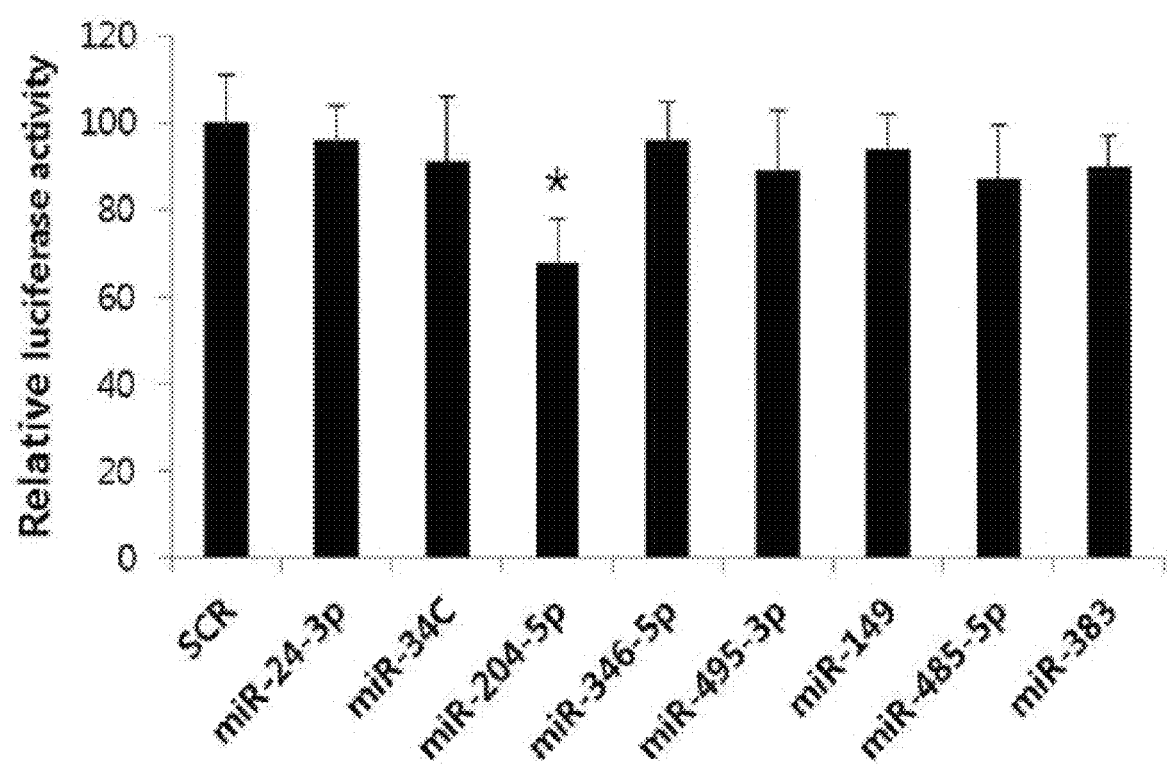
FIG. 3 illustrates data on the selection of miRNAs involved in EphB2.
Figure 4:
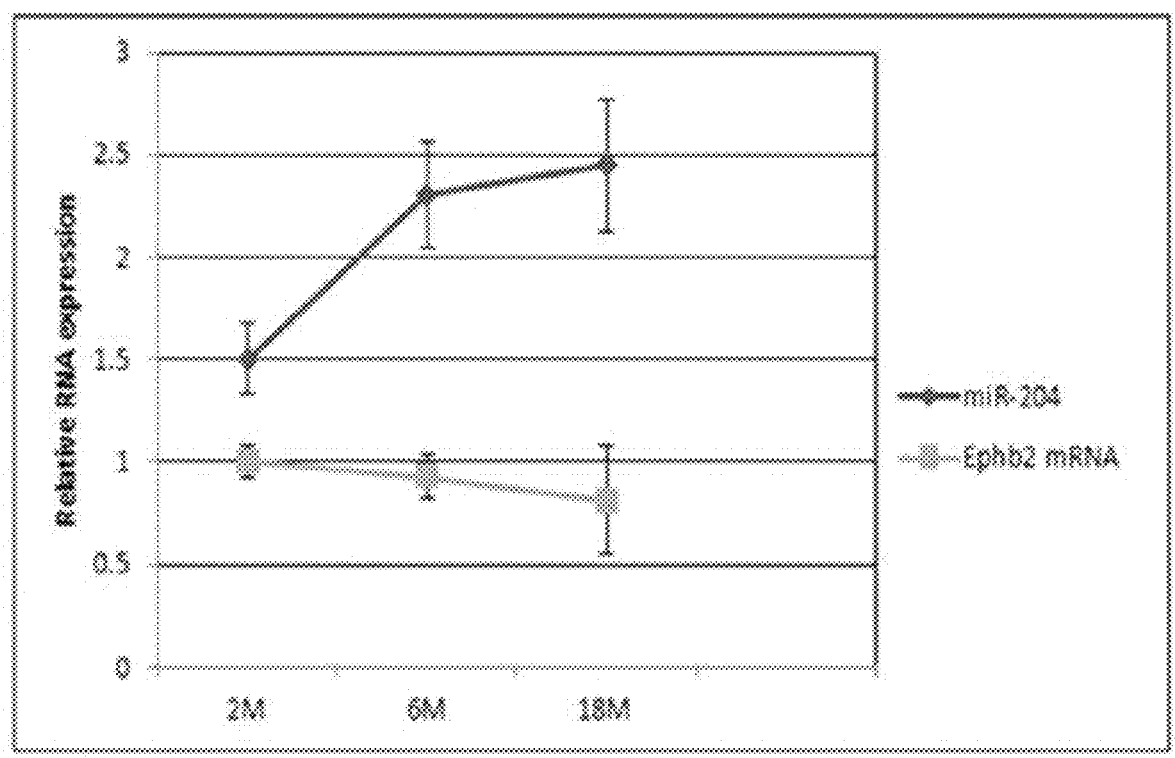
FIG. 4 illustrates data of relative RNA expression of miRNA204-5p and EphB2.

As shown in FIG. 3, in the present disclosure, 8 candidate miRNAs, which are miR-24-3p, miR-34C-5p, miR-204-5p, miR-346-5p, miR-495-3p, miR149-5p, miR-485-5p, miR-383-5p, having a binding site for 3'UTR (SEQ ID NO: 2) of EphB2 and having a decrease in expression more than 2-fold in 2 and 18 months rats were confirmed (MIMAT0000219, MIMAT0000381, MIMAT0000237, MIMAT0000597, MIMAT0003456, MIMAT0000159, MIMAT0003128, MIMAT0000748), and it was confirmed that of them, only miR-204-5p represented by the base sequence of SEQ ID NO: 1 inhibits EphB2 activity. In addition, as shown in FIG. 4, it was confirmed that mRNA expression of miR-204-5p and EphB2 are inversely correlated as aging progresses.

Figure 5A:
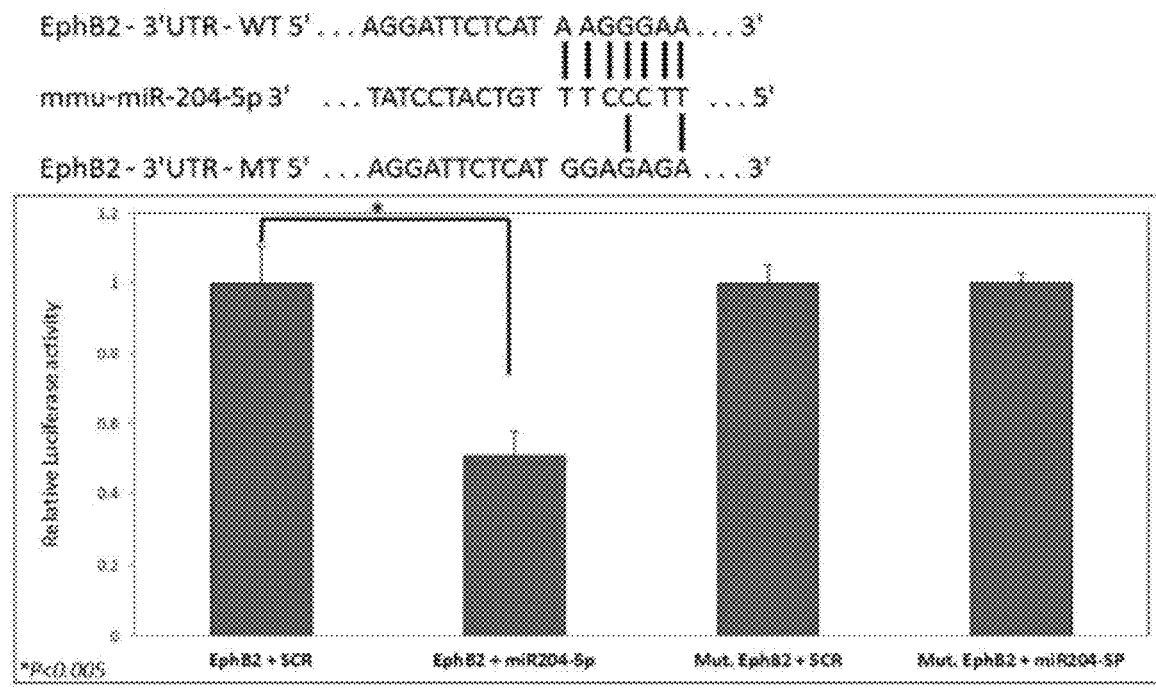
FIG. 5a illustrates EphB2 which is a target of miR-204-5p in neuron, and illustrates relative luciferase activity when miR-204-5p was treated with wild-type and mutated EphB2-3'UTR.
Figure 5B:
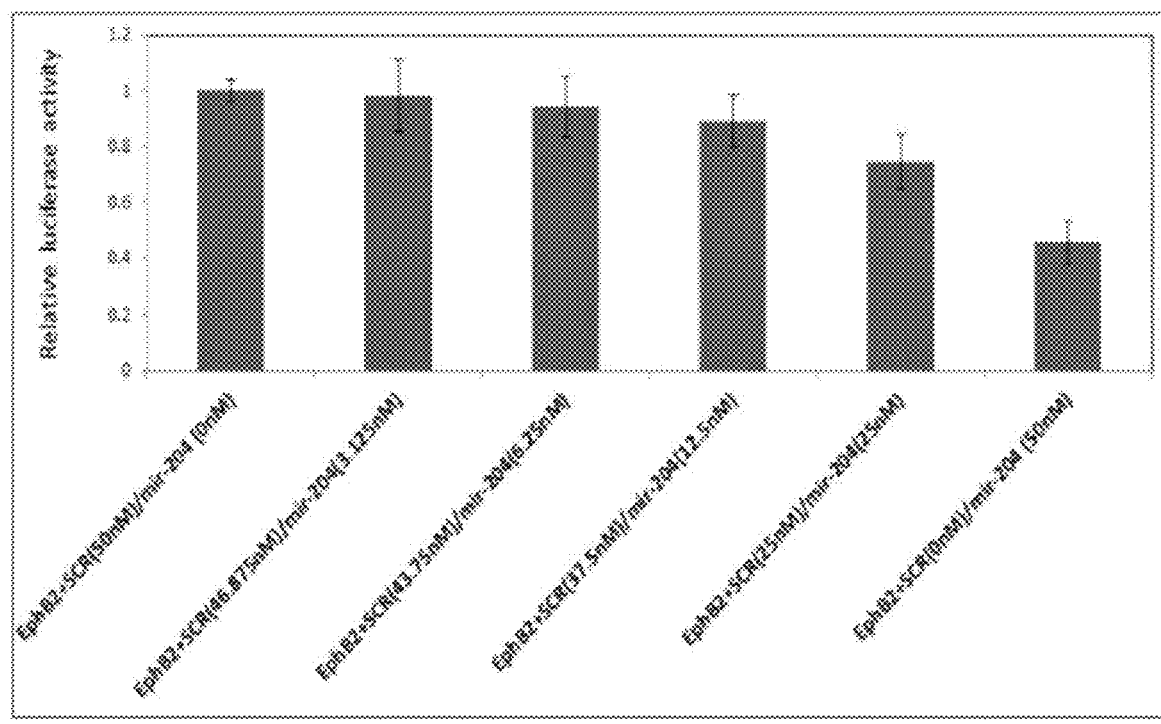
FIG. 5b illustrates data of the luciferase activity of miR-204-5p concentration-dependent EphB2-3'UTR in cultured hippocampal nerves.

In one embodiment of the present disclosure, to confirm whether miR-204-5p was specific to EphB2, the activities of wild-type EphB2-3'UTR-WT (AGGATTCTCATAAGGGAA (SEQ ID NO: 2)) and miR-204 binding site point mutated EphB2-3'UTR-MT (AGGATTCTCATGGAGAGA (SEQ ID NO: 3)) were compared. As shown in FIG. 5a, EphB2-3'UTR-WT and miR-204-5p were reacted, as a result, it was confirmed that the activity of EphB2 was abruptly decreased, on the other hand, that of EphB2-3'UTR-MT was not changed. In addition, as shown in FIG. 5b, it was confirmed that the activity of EphB2 was decreased depending as a miR-204-5p concentration-dependent manner.

Figure 5C:
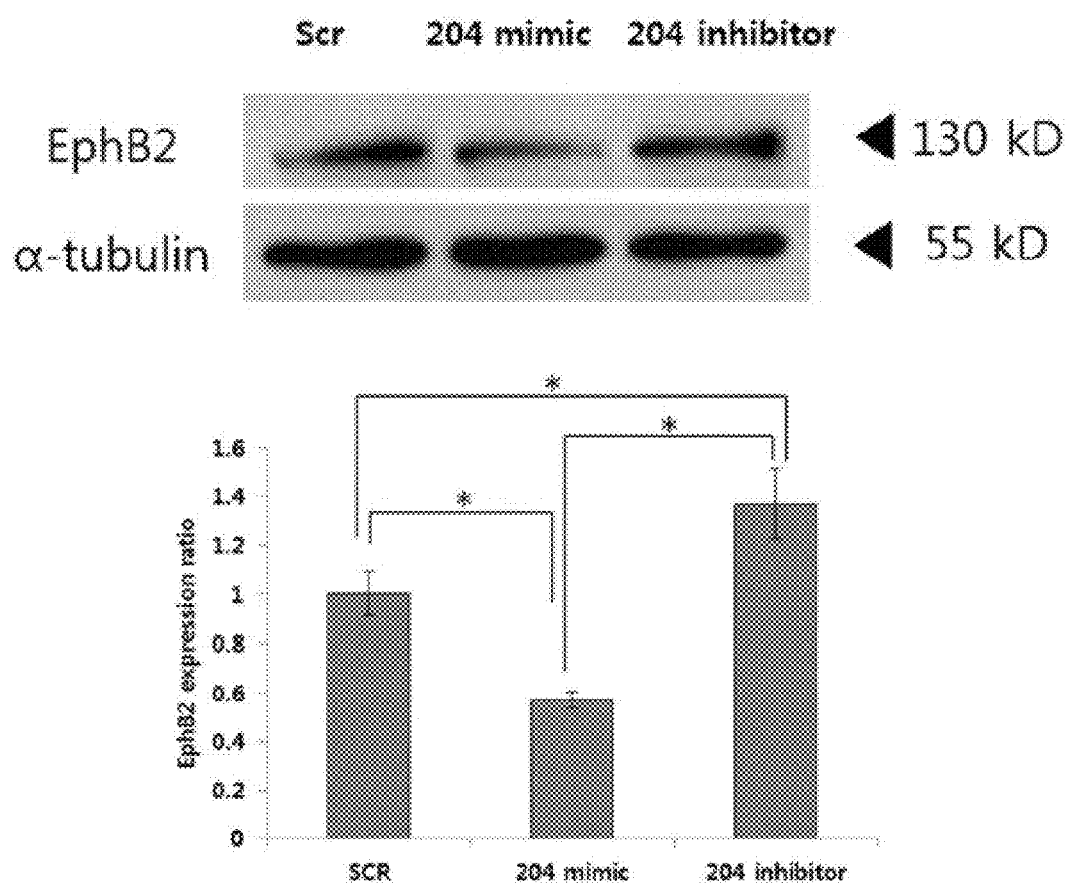
FIG. 5c illustrates data determined by western blotting of expression change of EphB2 when neurons were treated with miR-204 mimic and miR-204 inhibitor.

FIG. 5c illustrates, data confirmed changes in EphB2 protein expression by western blot when neurons were treated with miR-204 mimic and miR-204 inhibitor (5'AGGCAUAGGAUGACAAAGGGAA 3' (SEQ ID NO: 4)), it was confirmed that the expression amount of EphB2 was significantly decreased to 50% by miR-204, and when the miR-204 inhibitor was treated, it was confirmed that the expression amount of EphB2 was recovered to 130%. In other words, it was confirmed that EphB2 was a direct target of miR-204-5p in the present disclosure.

Figure 6:
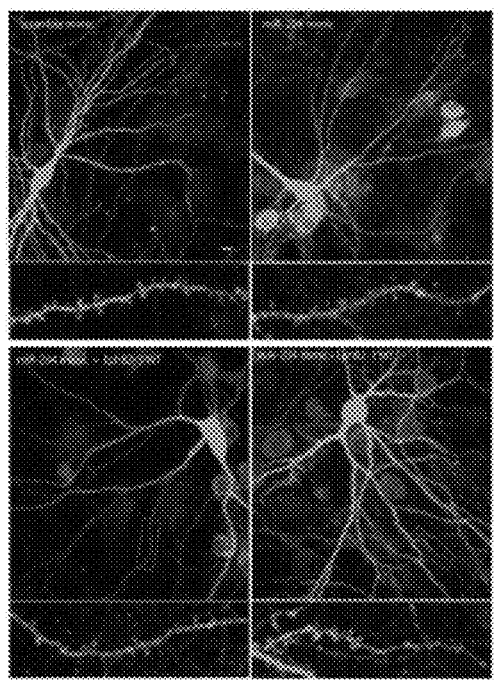
FIG. 6 illustrates data determined of whether a dendritic density is regulated by miR-204.
Figure 6:
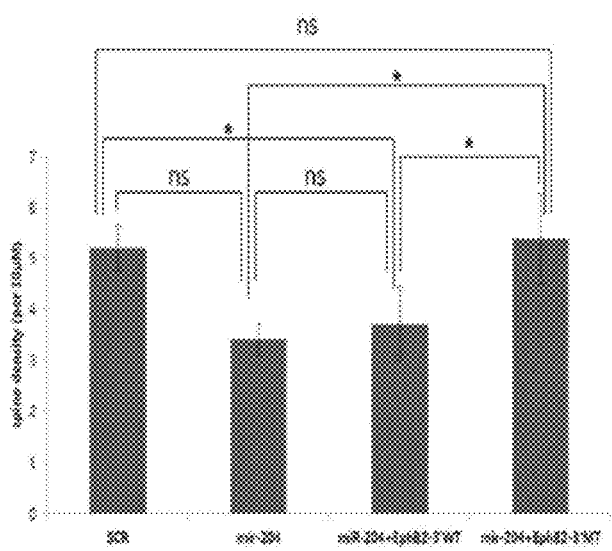

In one embodiment of the present disclosure based on the above results, the relationship between miR-204-5p and EphB2 in synaptic plasticity was examined. As shown in FIG. 6, the regulation degree of dendritic spine density by miR-204-5p was confirmed, as a result, it was confirmed that the over-expression of miR-204-5p decreased the spine density by 40% when compared with the control group scramble mimic (3.4 spine/10 um length, including 5.2 spine protrusion, p<0.001). When EphB2-3'UTR-WT and miR-204 mimic were simultaneously transfected (3.9 spine/10 um length, p>0.5), it was confirmed that there was no significant increase in spine density compared to miR-204 mimic (3.6 spine/10 um length, p<0.001) only infected neurons, on the other hand, when EphB2-3'UTR-MT and miR-204 mimic were simultaneously transfected (5.4 spine/10 nm length, p<0.001), it was confirmed that there was spine density of normal levels. In other words, the above result means that miR-204-5p regulates the dendritic spine density through the inhibition of EphB2.

In addition, since EphB2 is known to mediate NMDA receptors expressed on the cell surface of neurons, whether miR-204-5p affects the transport and location change of NMDA receptor subunits in the hippocampal nerves were examined.

Figure 7A:
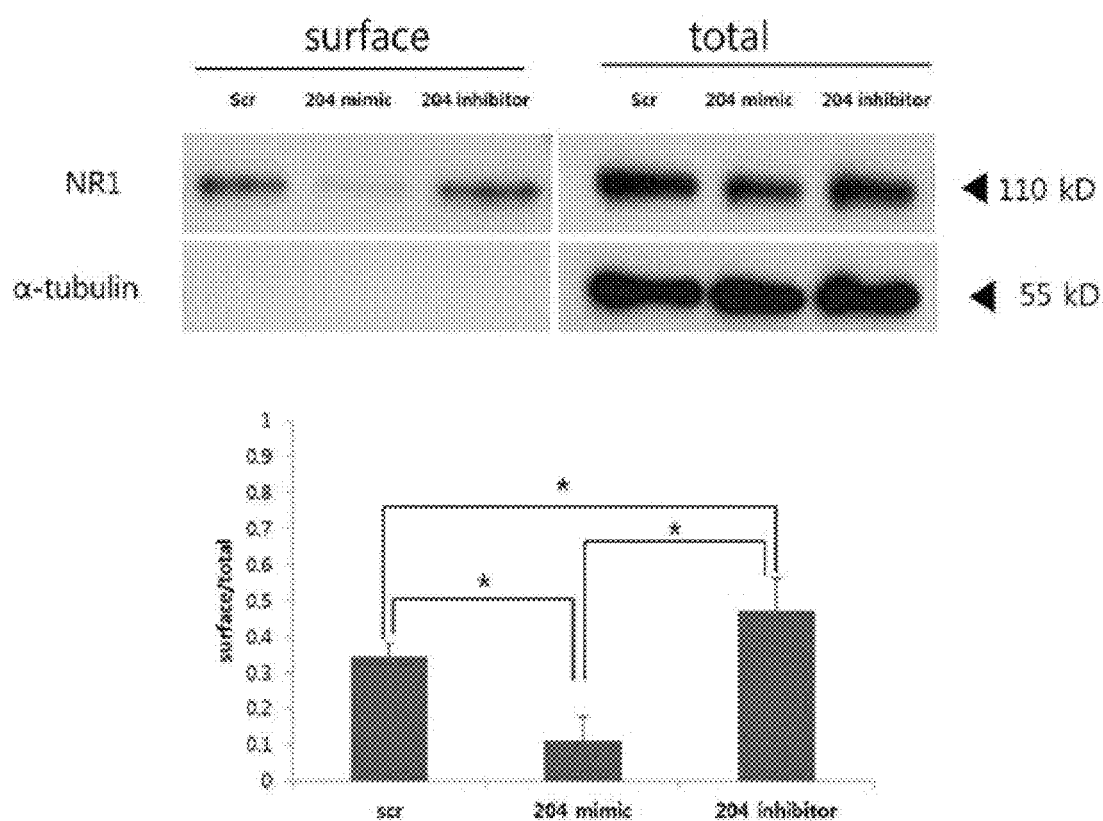
FIG. 7a illustrates data of surface expression degree of NR1 subunit of the NMDA receptor by miR-204. The biotinylated (surface) NR1 and total NR1 proteins in hippocampal nerves transformed with scramble (scr) on day 7 of culture, miR-204 mimic and miR-204 inhibitor were visualized by immunostaining using specific antibodies. Tubulin was used as a loading control group of the total protein, and the absence of tubulin indicates the effectiveness of the surface label. The bar graph illustrates the expression ratios of surface NR1 and total NR1 on day 7 of culture (* P<0.05, error bars: standard mean error).
Figure 7B:
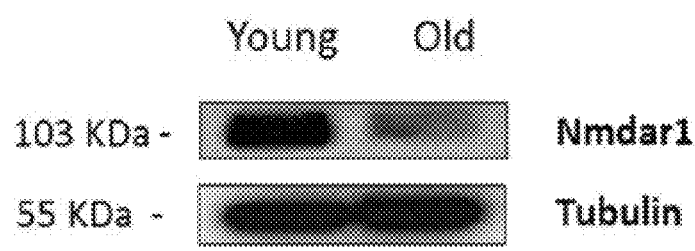
FIG. 7b illustrates data quantifying protein expression degree of the NMDA receptor NR1 subunit using western blot analysis from young and old hippocampal tissue. Protein band quantification and relative density were analyzed using image J software.
Figure 7B:
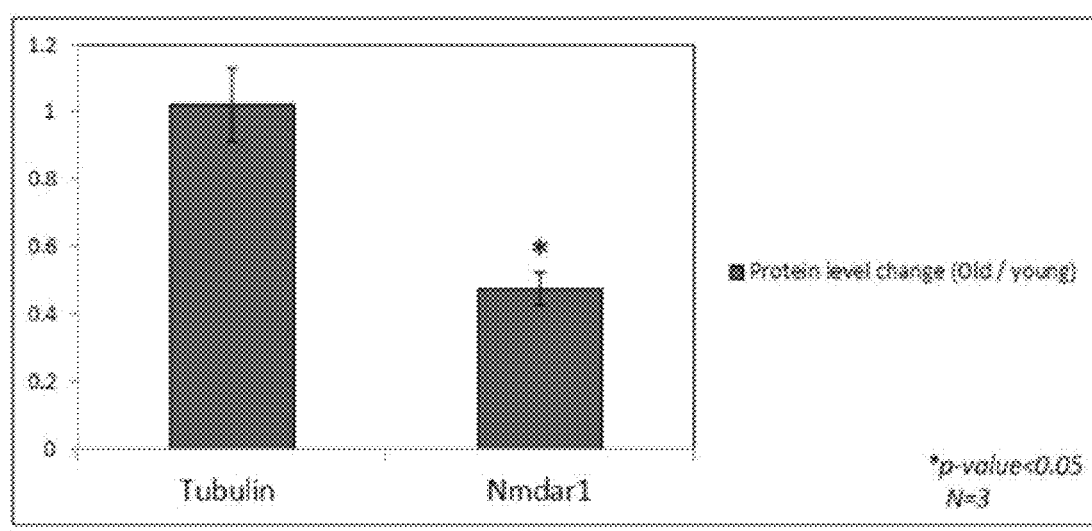

FIG. 7 illustrates data showing the surface expression regulation degree of NR1 subunit of NMDA receptor by miR-204, as a result of confirming the ratio of the cell surface NR1 protein/total NR1 protein, it was confirmed that the expression ratio of NR1 protein was significantly decreased on neuronal cell surface by miR-204, on the other hand, it was confirmed that the expression ratio of NR1 protein was significantly increased by the miR-204 inhibitor.

In addition, as shown in FIG. 7b, as a result of confirming the expression of the NMDA receptor NR1 subunit from the young (of 2 months mouse) and the old (of months mouse) hippocampal tissues, It was confirmed that the expression of total NR1 protein was decreased by about 50% in the aging process. The above means that the expression of neurons' cell surface and total NR1 protein was decreased as the expression of EphB2 in neurons is decreased by miR-204, In other words, since it was confirmed in the present disclosure that of the miRNAs up-regulated in the aging hippocampus, miR-204 accurately targets EphB2 an important regulatory receptor and educes EphB2 expression, and which causes neuronal surface expression of the NR1 subunit of the NMDA receptors in the hippocampal nerves to decrease and dendritic density resulting in a decrease, it was confirmed that the correlation between miR-204-5p and EphB2 or the correlation between miR-204-5p and NMDA receptor can be used to determine whether hippocampal function is reduced.

Further, the correlation between the miR-204-5p and EphB2 or the correlation between the miR-204-5p and the NMDA receptor can be utilized in a method for inhibiting decrease in functions of the hippocampus and a method for screening inhibitors of decrease in functions.

In other words, the present disclosure also relates to a method for inhibiting decrease in functions of hippocampus comprising: treating an agent which inhibits expression of miR-204-5p or inhibits an activity of miR-204-5p to increase an expression of a NMDA receptor.

The method can be applied to a decrease in hippocampal function caused by a decrease in an expression of a NMDA receptor or a general aging process.

In addition, the present disclosure can be applied to cognitive function improvement, memory damage inhibition/improvement, the treatment of various diseases resulting from decrease in hippocampal function.

The agent which inhibits expression of miR-204-5p or inhibits an activity of miR-204-5p may be an antisense oligonucleotide or an siRNA. In the present disclosure, preferably miR-204-5p represented by the base sequence of SEQ ID NO: 4 was used as an inhibitor, but oligonucleotides having a complementary sequence to miR-204-5p represented by the base sequence of SEQ ID NO: 1 can be used without limitation, and oligonucleotides capable of selectively binding only specific regions of miR-204-5p that specifically recognize 3'UTR of EphB2 can also be used without limitation.

It is characterized that the expression of EphB2 protein is increased by an agent which inhibits expression of miR-204-5p or inhibits an activity of miR-204-5p, which causes the expression of NMDA receptor in the hippocampal nerves increases. Preferably, it is characterized by an increase in the expression of the NR1 subunit among the NMDA receptor on the cell surface of neuron (nerve cell). In addition, it is characterized by the dendritic spine density in the hippocampal nerves is increased by the agent which inhibits expression of miR-204-5p or inhibits an activity of miR-204-5p.

As described above, it was confirmed that since the expression of EphB2 protein was increased by miR-204-5p inhibitor and the expression of NR1 subunit was increased in FIG. 5c and FIG. 7a, it was confirmed that the agent inhibiting an expression of miR-204-5p or inhibiting an activity of a miR-204-5p was treated to inhibit decrease in functions of the hippocampus.

The present disclosure also relates to a method for screening a decrease in functions of hippocampus inhibitor comprising: (a) treating a candidate substance which inhibits miR-204-5p expression or inhibits activity of miR-204-5p in human-derived hippocampal nerves; and (b) confirming whether expression of the NMDA receptor is increased on the surface of the neuron.

It is characterized that of the candidate substances, a substance that increases the expression of the NMDA receptor is selected. In particular, it can be confirmed whether the expression of the NR1 subunit is increased in the NMDA receptor.

In addition, in step (b), by further confirming the increased expression of EphB2 protein, a candidate substance which increases the expression of EphB2 protein can be selected.

Further, the present disclosure relates to a pharmaceutical composition for preventing or treating decrease in functions of hippocampus, comprising: an agent which inhibits expression of miR-204-5p represented by the base sequence of SEQ ID NO: 1 or inhibits an activity of miR-204-5p.

In addition, the present disclosure provides to an use for using of an agent which inhibits expression of miR-204-5p represented by the base sequence of SEQ ID NO: 1 or inhibits an activity of miR-204-5p for preventing or treating decrease in functions of hippocampus.

In addition, the present disclosure provides to a method for preventing decrease in functions of hippocampus, comprising: administering an agent which inhibits expression of miR-204-5p represented by the base sequence of SEQ ID NO: 1 or inhibits an activity of miR-204-5p to an individual in need thereof in a pharmaceutically effective amount.

Further, the present disclosure provides to a method for treating decrease in functions of hippocampus, comprising: administering an agent which inhibits expression of miR-204-5p represented by the base sequence of SEQ ID NO: 1 or inhibits an activity of miR-204-5p to an individual in need thereof in a pharmaceutically effective amount.

The composition of the present disclosure can Improve cognitive impairment, and prevent and treat various diseases related to abnormality of hippocampal function due to aging. In addition, since the composition of the present disclosure inhibits an activity of miR-204-5p and increases the expression of NMDA receptor which is a surface protein of hippocampal nerves, it can be applied to the prevention or treatment of various diseases such as stroke, schizophrenia and the like, which are caused by decrease in an expression of a NMDA receptor or abnormal function.

The pharmaceutical composition comprising an agent which inhibits expression of miR-204-5p represented by the base sequence of SEQ ID NO: 1 or inhibits an activity of miR-204-5p for preventing and treating decrease in functions of hippocampus according to the present disclosure may further include other agents capable of improving hippocampal function.

Hereinafter, the present disclosure will be described in detail, which can be readily carried out by a person having ordinary skills in the art to which the present disclosure pertains, with reference to the preferred embodiments. However, the present disclosure may be embodied in many different forms and should not be construed as limited to the embodiments set forth herein.

Example 11 Analysis of Small RNA (Small RNA) Profiling Related to Hippocampal Aging Process In the present disclosure, small RNA (smRNA or sRNA, hereinafter referred to as sRNA) profiling was performed in male rats at 2 months, 6 months and 18 months to understand the miRNA mediating the regulation of the hippocampal aging process.

1-1: Animal Preparation and Tissue Collection

General wild-type male C57BL/6J rats of three different ages, 2 months, 6 months and 18 months, were obtained from Korea Research Institute of Bioscience & Biotechnology-Institutional animal care and use committee (KRIBB-IACUC)

Normal rats without tumor or disease signs sacrifices, and hippocampal tissues were immediately dissected from therefrom and stored frozen in liquid nitrogen. Health status of the normal rats was confirmed through a series of serological tests and eight hippocampal tissues were obtained from four rats at each stage. All animals were maintained under "specific pathogens free (SPF)" conditions and all animal studies were performed according to the approval guidelines provided by KRIBB-IACUC.

1-2: Preparation of RNA

RNA extraction and a quality control method were performed using standard protocols.

First, the frozen tissues were homogenized and then extracted with phenol. The obtained RNA pellet was dissolved in nuclease free water and stored at −80° C. until use.

RNA purity and concentration were analyzed using a NanoDrop 2000 spectrophotometer (Thermo Scientific, USA). All samples showed a A260/A280 ratio of 2 or higher and an A260/A230 ratio of 1.9 or higher in nuclease free water.

RNA integrity was analyzed using a Bio-analyzer Nano 6000 chip (Agilent Technologies, USA) to confirm the quality of the RNA. RNA samples with correct 18S/28S and RNA Integrity Number (RIN) values higher than 8 were used for further experiments.

1-3: Extraction of Small RNA and Construction of cDNA Library

Small RNA (hereinafter referred to as small RNA) was extracted using the Pure Link Micro-to-Midi Total RNA Purification System kit (Invitrogen, USA) and miRNeasy mini kit (Qiagen, USA). The sRNA was purified at all stages of rat hippocampal tissue and prepared for Illumina sequencing according to manufacturer's recommendations.

At each stage, 10 μg of sRNA isolated from rat hippocampal tissues of 4 rats was subjected to electrophoresis on a 15% TBE-urea PAGE gel. Then, the fraction of the line containing the RNA molecule which length of the sRNA is between 18 and 30 nucleotides was cleaved from the gel, and the RNA was separated from the gel fragment and ethanol precipitated. The separated sRNA was synthesized as cDNA by attaching 5 'and 3' adapters (illumina truseq kit, cat No: FC-121-3001) and reverse transcription according to manufacturer's protocol. The obtained cDNA was subjected to PCR amplification using an illumina primer (illumina truseq kit, cat No: FC-121-3001), and the PCR amplification product was electrophoresed and cleaved from the polyacrylamide gel, precipitated with ethanol and separated. Each cDNA library was sequenced using an illuminance sequence analysis technique.

1-4: Deep Sequencing—Next-Generation Sequencing

In the present disclosure, miRNA profiles for three stages of rat hippocampal tissues were characterized using Illumina deep sequencing Hi-seq2000.

In all age groups, the sRNA sample library performed single end sequencing with a read length (length that can be read at one time) of 50 nt (nucleotide). The index base sequence and the 3'adapter base sequence were removed from the reading, and the sequence containing the adapter dimers, mitochondria or ribosome sequence was discarded. In addition, the sequence those containing homopolymers or shorter than 14 nt were removed from reading.

The results of the readings were subjected to align raw sequences using a software program of cufflink (Johns Hopkins University) and Top-Hat (Johns Hopkins University), After mapping with reference to the murine genome (Mus_musculus.NCBIM37.55), the sequence read number corresponding to known miRNA to confirm the type of mature miRNA was determined by the sequence that perfectly matched the database of known miRNAs (miR Base release version 16).

1-5: Analysis of miRNA Expression Profile

Raw data (read for each miRNA) was normalized to reads per million (RPM, miRNA counts/total counts of each sample×1 million) and less than 10 readings of miRNA for each sample. In addition, 1 is added to the RPM value to facilitate Log 2 conversion.

The filtered data were transformed by logarithm, differentially expressed miRNA was regulated the difference between 2 months group at the time of regulate and 6 months and 18 months groups to Fold change >|2.0|.

As a result, as shown in FIG. 1a, it was confirmed that of the total 269 miRNAs in the hippocampus, 80 miRNAs exhibit fold change values of 2.0 or higher for any two of the three different time periods.

As shown in FIG. 1b, when sporadic volume configurations of 269 miRNAs in hippocampus expressed during normal aging progression (between 2 months and 18 months), 19 miRNAs were decreased more than 2-fold in expression, on the other hand, 36 miRNAs were increased more than 2 fold in expression.

1-6: Real-Time Quantitative PCR Assay

To confirm the significance of sRNA data, twelve miR-NAs having fold change values of 2.0 or greater in rats of 2 and 18 months were randomly selected (increase in expression: 5, decrease in expression: 7) and analyzed by real-time quantitative polymerase chain reaction (real-time quantitative PCR; qPCR).

Selected miRNAs are mmu-miR-191-5p, mmu-miR-342-3p, mmu-miR-99b-5p, mmu-miR-139-5p, mmu-miR-433-3p, mmu-miR-1839-5p, mmu-miR-144-5p, mmu-miR-125b-1-3p, mmu-miR-125b-2-3p, mmu-miR-298-5p and mmu-miR-411-5p. (MIMAT0000221, MIMAT0000590, MIMAT0000132, MIMAT0000656, MIMAT0001420, MIMAT0009456, MIMAT0016988, MIMAT0004669, MIMAT0004529, MIMAT0000376, MIMAT0004747)

First, Invitrogen NCode™ miRNA First strand cDNA module was used to synthesize cDNA by reverse transcription mature miRNA in total RNA isolated from the above.

Total RNA and miRNA (1 μg each) were used to generate cDNA templates according to the manufacturer's instructions. The reaction solution was reacted in a Bio-Rad Thermal Cycler (Bio-Rad, USA) at a total reaction volume of 20 μl. PCR was performed using Bio-Rad real-time PCR system (CFX-96), Each primer design for miRNA was performed using Primer Blast interface and PrimerBank. All reactions were performed by dispensing into two sets (using universal reverse primers for miRNAs) of 96-well plates with the SYBR Green Mix and each primer set.

TABLE 2

| Term | Gene Count | P-Value | Benjamin Score |
|---|---|---|---|
| Pathway in cancer | 136 | 2.7E-23 | 4.9E-21 |
| Axon quidance | 69 | 4.5E-18 | 4.1E-06 |
| Insulin signaling pathway | 67 | 3.7E-15 | 2.2E-13 |
| Regulation of actin cytoskeleton | 89 | 2.3E-14 | 1.0E-12 |
| Focal adhesion | 83 | 4.6E-14 | 1.7E-12 |
| Colorectal cancer | 49 | 3.6E-13 | 1.1E-11 |
| Adherens junction | 43 | 9.0E-13 | 2.3E-11 |
| MAPK signaling pathway | 98 | 1.8E-12 | 4.1E-11 |
| Wntsignaling pathway | 63 | 5.1E-11 | 1.0E-9 |
| Endocytosis | 75 | 8.7E-10 | 1.6E-8 |

As a result, various biological effects were derived as shown in Table 2, cancer-related pathways were expected to be significantly present, however the follow-up study was carried out with a focus on the axon guidance pathway ($P=4.5E-18$), which has relatively little research in the aspect of aging. As the schematic diagram of the axon guidance pathway illustrated in FIG. 2a, in the present disclosure, the relationship between the activity of Eph/ephrin and miRNA was examined.

TABLE 1

| Target | | Sequence (5'-3') | SEQ ID NO. |
|---|---|---|---|
| mmu-miR-191-5p | forward | CAACGGAAUCCCAAAAGCAGCUG | SEQ ID NO: 5 |
| mmu-miR-342-3p | forward | UCUCACACAGAAAUCGCACCCGU | SEQ ID NO: 6 |
| mmu-miR-99b-5p | forward | CACCCGUAGAACCGACCUUGCG | SEQ ID NO: 7 |
| mmu-miR-139-5p | forward | UCUACAGUGCACGUGUCUCCAG | SEQ ID NO: 8 |
| mmu-miR-433-3p | forward | AUCAUGAUGGGCUCCUCGGUGU | SEQ ID NO: 9 |
| mmu-miR-1839-5p | forward | AAGGUAGAUAGAACAGGUCUUG | SEQ ID NO: 10 |
| mmu-miR-144-5p | forward | GGAUAUCAUCAUAUACUGUAAGU | SEQ ID NO: 11 |
| mmu-miR-125b-1-3p | forward | ACGGGUUAGGCUCUUGGGAGCU | SEQ ID NO: 12 |
| mmu-miR-125b-2-3p | forward | ACAAGUCAGGUUCUUGGGACCU | SEQ ID NO: 13 |
| mmu-miR-298-5p | forward | GGCAGAGGAGGGCUGUUCUUCCC | SEQ ID NO: 14 |
| mmu-miR-411-5p | forward | UAGUAGACCGUAUAGCGUACG | SEQ ID NO: 15 |
| universal miRNA | reverse | GTGCAGGGTCCGAGGT | SEQ ID NO: 16 |

As a result, as shown in FIG. 1c, it was confirmed that it coincided with the sRNA profiling data, it was confirmed that sRNA profiling can reflect the entire miRNA expression pattern in hippocampal tissue.

[Example 2] Pathway Analysis of Target Gene

All lists of expected target genes for differentially expressed miRNAs according to the aging process were entered into gene functional analysis of DAVID, Kyoto Encyclopedia of a Genes and Genomes (KEGG) and Ingenuity Pathway Analysis (Ingenuity® Systems) with limited basic parameters for the results of rat species.

[Example 3] Determination of Eph/Ephrin Pathway Regulation by Aging 3-1: Determination of mRNA Expression In the present disclosure, qPCR analysis was performed to examine how the expression of Eph/ephrin subfamily changes by aging.

First, PrimeScript™ RT reagent Kit (Promega ImPromm-II Reverse Transcription System) was used to synthesize cDNA by reverse transcription of RNA of the rat hippocampal tissues of each stage separated in Example 1. Total RNA (1 μg each) was used to generate cDNA templates according to the manufacturer's instructions. The reaction solution was reacted in a Bio-Rad Thermal Cycler (Bio-Rad, USA) at a total reaction volume of 20 μl.

PCR was performed using Bio-Rad real-time PCR system (CFX-96), Each primer design for miRNA was performed using Primer Blast interface and PrimerBank. All reactions were performed by dispensing into two sets of 96-well plates with the SYBR Green Mix and each primer set.

TABLE 3

| Target | | Sequence (5'-3') | SEQ ID NO. |
|---|---|---|---|
| EphA1 | forward | AGGAAGTCACTCTAATGGACACA | SEQ ID NO: 17 |
| | reverse | CCTCACTCCACCCAGTCTCT | SEQ ID NO: 18 |
| EphA2 | forward | GCACAGGGAAAGGAAGTTGTT | SEQ ID NO: 19 |
| | reverse | CATGTAGATAGGCATGTCGTCC | SEQ ID NO: 20 |
| EphA3 | forward | CATGGGTGGGAAGAGATCAGT | SEQ ID NO: 21 |
| | reverse | GATGCTCTCGGAATTTGACGC | SEQ ID NO: 22 |
| EphA4 | forward | TGGAATTTGCGACGCTGTCA | SEQ ID NO: 23 |
| | reverse | CACTTCCTCCCACCCTCCTT | SEQ ID NO: 24 |
| EphB1 | forward | CCTCCTCCTATGGACTGCCC | SEQ ID NO: 25 |
| | reverse | AAGGCCGTGAAGTCTGGGATA | SEQ ID NO: 26 |
| EphB2 | forward | GCGGCTACGACGAGAACAT | SEQ ID NO: 27 |
| | reverse | GGCTAAGTCAAAATCAGCCTCA | SEQ ID NO: 28 |
| EphB3 | forward | CATGGACACGAAATGGGTGAC | SEQ ID NO: 29 |
| | reverse | GCGGATAGGATTCATGGCTTCA | SEQ ID NO: 30 |
| EphrinA1 | forward | CTTCACGCCTTTTATCTTGGGC | SEQ ID NO: 31 |
| | reverse | TGGGGATTATGAGTGATTTTGCC | SEQ ID NO: 32 |
| EphrinA2 | forward | CGATACGCAGTCTACTGGAAC | SEQ ID NO: 33 |
| | reverse | GGTAGTCGTTGATGCTCACCT | SEQ ID NO: 34 |
| EphrinA3 | forward | CGTGCAGGTGAACGTGAAC | SEQ ID NO: 35 |
| | reverse | GTAACGCTGGAACTTCTCGGA | SEQ ID NO: 36 |
| EphrinB1 | forward | TGTGGCTATGGTCGTGCTG | SEQ ID NO: 37 |
| | reverse | CCAAGCCCTTCCCACTTAGG | SEQ ID NO: 38 |
| EphrinB2 | forward | ATTATTTGCCCCAAAGTGGACTC | SEQ ID NO: 39 |
| | reverse | GCAGCGGGGTATTCTCCTTC | SEQ ID NO: 40 |
| EphrinB3 | forward | TGCTGCTGTTAGGTTTTGCG | SEQ ID NO: 41 |
| | reverse | CTGAGGATAAAGCACGTAACCG | SEQ ID NO: 42 |
| Rgs | forward | AGTGCAGGATGCAGGTCAAC | SEQ ID NO: 43 |
| | reverse | GAAAGAAGAAGTGCTCGTGGAA | SEQ ID NO: 44 |
| RhoA | forward | AGCTTGTGGTAAGACATGCTTG | SEQ ID NO: 45 |
| | reverse | GTGTCCCATAAAGCCAACTCTAC | SEQ ID NO: 46 |
| Rock2 | forward | TTGGTTCGTCATAAGGCATCAC | SEQ ID NO: 47 |
| | reverse | TGTTGGCAAAGGCCATAATATCT | SEQ ID NO: 48 |
| cdk5 | forward | CCCTGAGATTGTGAAGTCATTCC | SEQ ID NO: 49 |
| | reverse | CCAATTTCAACTCCCCATTCCT | SEQ ID NO: 50 |
| Mapk1 | forward | GGTTGTTCCCAAATGCTGACT | SEQ ID NO: 51 |
| | reverse | CAACTTCAATCCTCTTGTGAGGG | SEQ ID NO: 52 |
| Rasa1 | forward | TGTGGTGATTACTACATTGGTGG | SEQ ID NO: 53 |
| | reverse | CGCCTTCTATCTTCTACTGGCTC | SEQ ID NO: 54 |
| Pak2 | forward | AACGGAGAGCTAGAAGACAAGC | SEQ ID NO: 55 |
| | reverse | TGGAACAGAAGGCAAAGGTTT | SEQ ID NO: 56 |
| Fyn | forward | ACCTCCATCCCGAACTACAAC | SEQ ID NO: 57 |
| | reverse | CGCCACAAACAGTGTCACTC | SEQ ID NO: 58 |
| Met | forward | GTGAACATGAAGTATCAGCTCCC | SEQ ID NO: 59 |
| | reverse | TGTAGTTTGTGGCTCCGAGAT | SEQ ID NO: 60 |
| Actin | forward | GGCTGTATTCCCCTCCATCG | SEQ ID NO: 61 |
| | reverse | CCAGTTGGTAACAATGCCATGT | SEQ ID NO: 62 |

As a result, as shown in FIG. 2b, it was confirmed in the aging process that 9 molecules of the target molecules in the Eph/ephrin subfamily were reduced in expression, 13 molecules of the target molecules were not observed any significant change, the expression of was homolog gene family (RhoA, member A) was only increased. In particular, EphA1 and EphB2, two ephrin receptors known to regulate synaptic plasticity, were found to be approximately 30% and 25% decreased in mRNA expression, respectively.

In addition, as shown in FIG. 2c, the fold change values of the target mRNAs involved in the Eph/ephrin signal in hippocampal tissues of 2 and 18 months rats were analyzed using qPCR. As a result, it was confirmed that EphrinB3, which was a single ephrin subunit, and EphA1, EphA2, EphA4 and EphB2, which were four ephrin receptor subunits, were decreased mRNA expression by 25 to 60% ($p<0.05$), on the other hand, RhoA mRNA was increased expression by 50% ($p<0.05$).

3-2: Determination of Protein Expression

To confirm whether the protein expression of the above molecules also changed with aging, the degree of protein expression for RhoA, EphA4 and EphB2 was confirmed.

Western blots were performed on each hippocampal tissue sample according to the Abcam® Western blotting protocol. First, 20 to 30 μg of the total lysate was taken, electrophoresed on a 5% sodium dodecyl sulfate/5-20% gradient polyacrylamide gel (SDS-PAGE), and electro-transferred to a nitrocellulose membrane.

The blots were hybridized with first antibody and then treated with second antibody, and each antibody was diluted in a Tris-buffered saline solution containing 5% dry milk. Hybridized bands were confirmed using an enhanced chemiluminescence (ECL) detection system (Describe the used ECL solution and measuring instrument information).

α-Tubulin (AbClon; AbC-2001), RhoA (abcam; ab68826), EphB2 (R&D systems; H00002048-M03) and EphA4 (Abnova; H00002043-M02) were used as the first antibodies and a peroxidase-conjugated second antibody (Jackson ImmunoResearch Laboratories) was used.

Protein band expression of western blot was quantified using image-J software (ImageJ 1.46).

As a result, as shown in FIG. 2d, EphA4 ($p<0.005$, n=4) and EphB2 ($p<0.005$, n=4) decreased protein expression by 60% and 30%, respectively, RhoA ($P=0.005$, n=4) increased protein expression up to 150%.

[Example 4] Selection of miRNA Targeting EphB2 the Present Disclosure Seeks to Select miRNA Targeting EphB2, which Expression is Markedly Regulated in the Aging Period First, 8 candidate miRNAs, which are miR-24-3p, miR-34C-5p, miR-204-5p, miR-346-5p, miR-495-3p, miR149-5p, miR-485-5p, miR-383-5p, having a decrease in expression more than 2-fold in 2 and 18 months rats were selected (MIMAT0000219, MIMAT0000381, MIMAT0000237, MIMAT0000597, MIMAT0003456, MIMAT0000159, MIMAT0003128, MIMAT0000748).

To test the competence of miRNA for inhibition of EphB2, Luciferase assay an analysis method was used. First, the luciferase-EphB2-3'UTR reporter construct (Promega) represented by the base sequence of SEQ ID NO: 4 and the candidate miRNA mimic were transfected into HEK293 cells.

The cells were inoculated into 24 wells so as to be 20,000 cells/well and cultured for 24 hours. luciferase-EphB2-3'UTR reporter and miRNA mimic were mixed with 2 μl of lipofectamine so as to be 0.5 μg, respectively, and were transfected for 4 hours. Then 50 μg of any luciferase reaction solution was added to each well, and luciferase activity was measured using Promega instrument.

As shown in FIG. 3, it was confirmed that only miR-204-5p represented by the base sequence of SEQ ID NO: 1 inhibits EphB2 activity.

To more particularly understand the miR-204-5p and EphB2 relationships. As a result, mRNA expression of miR-204-5p and EphB2 in the sRNA profile results of Example 1 were examined, as a result, as shown in FIG. 4, it was confirmed that mRNA expression of miR-204-5p and EphB2 are inversely correlated as aging progresses.

[Example 5] Determination of miR-204-5p Specificity for EphB2

In the present disclosure, to confirm whether miR-204-5p was specific to EphB2, the activity of wild type EphB2-3'UTR-WT (SEQ ID NO: 2) and The EphB2-3'UTR-MT (SEQ ID NO: 3) in which the miR-204 binding site was point mutated was compared.

The luciferase assay was performed in the same manner as in Example 4, and a scramble mimic (5'GGUUCGUACGUACACUGUUCA3', SEQ ID NO: 64, was used as a control group.

As shown in FIG. 5a, when EphB2-3'UTR-WT and miR-204-5p were reacted, it was confirmed that the activity of EphB2 was abruptly decreased, on the other hand, there is no activity change in the case of EphB2-3'UTR-MT.

To confirm the change of EphB2 activity according to the miR-204-5p concentration, Transformation was performed in the same manner as above for 0 nM, 3.125 nM, 6.25 nM, 12.5 nM, 25 nM and 50 nM concentrations, and the luciferase activity was measured, and the control group scramble was treated with 50 nM, 25 nM, 12.5 nM, 6.25 nM, 3.125 nM and 0 nM to make the amount of material to be transformed equal.

As a result, it was confirmed that the activity of EphB2 was decreased depending as a miR-204-5p concentration-dependent manner.

[Example 6] Confirmation of Change in EphB2 Protein Expression by miR-204-5p

In the present disclosure, change in EphB2 protein expression y miR-204-5p was confirmed using western blot.

First, the dissociated hippocampal nerves were isolated from wild-type rat pups (stage P0). Neurons were inoculated on poly-lysine coated cover glasses (glass coverslips, 18 mm; Bellco Glass, USA) in 12-well plates, and then were maintained in Neurobasal medium containing B27 (Invitrogen, USA), glutamine (Sigma-Aldrich, USA) and penicillin-streptomycin (Sigma-Aldrich, USA), and then 70,000 cells were inoculated into each well, and then cultured in condition of 5% CO2, and 37% humidity.

The miR-204 mimic and miR-204 inhibitors (AGG-CAUAGGAUGACAAAGGGAA, SEQ ID NO: 65) were transformed on day 14 of culture, and the calcium phosphate method was used for transformation of neurons.

Cells were cultured in condition of 5% CO2 and 37° C. with moisture for 7 days after the transformation, cells were obtained, and the cells were agitated for 4 to 60 minutes using a RIPA buffer containing protease inhibitor to dissolve the cells. And the cells were briefly sonicated twice and centrifuged at 13,000 rpm for 4 to 15 minutes to separate the proteins. The separated proteins were subjected to western blotting in the same manner as in Example 3-2.

As a result, as shown in FIG. 5c, it was confirmed that the expression amount of EphB2 was significantly decreased to 50% by miR-204, and when the miR-204 inhibitor was treated, it was confirmed that the expression amount of EphB2 was recovered to 130%. In other words, it was confirmed that EphB2 was a direct target of miR-204-5p in the present disclosure.

[Example 7] Regulation of Dendritic Spine Density Through EphB2 Inhibition of miR-204-5p In the present disclosure, the relationship between miR-204-5p and EphB2 in synaptic plasticity was examined.

First, 1) scramble mimic, 2) miR-204 mimic, 3) EphB2-3'UTR-WT and miR-204 mimic, 4) EphB2-3'UTR-MT and miR-204 mimic were each transformed with the hippocampal nerves cultured for 14 days in the same manner as in Example 6, and then dendritic spine density was observed using a method for immunocytochemistry.

Neurons were treated with 4% paraformaldehyde/4% sucrose PBS and fixed at room temperature for 10 minutes. Cells were washed three times with PBS, treated with PBS containing 0.1% triton X-100 and permeabilized at room temperature for 10 minutes, blocked with 5% BSA in PBS, treated with PBS containing 5% BSA and blocked. Then, the cells were treated with Rabbit anti-GFP (Abcam: 1:1000) first antibody and reacted overnight at 4, washed three times with PBS containing 1% BSA, and treated with Alexa-488 conjugated second antibody (1:1,000, Life technologies) and reacted at room temperature for 1 hour.

Transformed neurons were randomly selected for quantitative analysis from each coverslip in multiple assays, and images were captured with LSM 760 using a 63× object glass. Dendrites were quantitatively analyzed from 50-200 µM cell body. Only second and third dendrites were used for quantitative analysis. All morphological experiments were repeated at least three times (n=10-20 individual experiments). The protrusion, which contained a bulbous head larger than the base, was measured with protrusions of the vertebral-head.

As shown in FIG. 6, it was confirmed that the overexpression of miR-204-5p decreased the spine density by 40% when compared with the control group scramble mimic (3.4 spine/10 um length, including 5.2 spine protrusion, p<0.001).

When EphB2-3'UTR-WT and miR-204 mimic were simultaneously transfected (3.9 spine/10 um length, p>0.5), it was confirmed that there was no significant increase in spine density compared to miR-204 mimic (3.6 spine/10 um length, p<0.001) only infected neurons, on the other hand, when EphB2-3'UTR-MT and miR-204 mimic were simultaneously transfected (5.4 spine/10 nm length, p<0.001), it was confirmed that there was spine density of normal levels.

[Example 8] Regulation of Cell Surface Expression of NMDA Receptor by EphB2 Inhibition of miR-204-5p Since EphB2 is known to mediate NMDA receptors expressed on the cell surface of neurons, whether miR-204-5p affects the transport and location change of NMDA receptor subunits in hippocampal nerves were examined.

First, it was prepared that 1) scramble mimic, 2) miR-204 mimic, 3) EphB2-3'UTR-WT and miR-204 mimic, 4) EphB2-3'UTR-MT miR-204 mimic were each transformed with the hippocampal nerves cultured for 14 days in the same manner as in Example 6, and cultured in condition of 5% CO2 and 37% for 7 days.

Biotinylation assay need to be performed to analyze proteins expressed on the cell surface.

The transformed mouse first hippocampal nerves were washed twice with cold PBS solution on ice, and cells were reacted on ice for 30 minutes in PBS solution containing 1 mg/ml sulfo-NHS-SS-Biotin (Pierce Protein Research Products). And then, to remove unattached biotin, the cells were washed with PBS solution containing 100 mM glycine, washed again with PBS solution, and the cells were agitated for 4 to 60 minutes using a RIPA buffer containing protease inhibitor to dissolve the cells. And the cells were briefly sonicated twice and centrifuged at 13,000 rpm for 4 to 15 minutes The total protein concentration was determined by taking 10% of the cell lysate and the remaining cell lysate (about 200 µg) was reacted with avidin agarose beads (Pierce, USA) for 25 to 60 minutes.

The separated proteins were washed 3 times with PBS, boiled with 2× sample buffer, and then subjected to western blotting with 20 µg of surface protein and total soluble protein.

The blots were hybridized with first antibody and then treated with second antibody, and each antibody was diluted in a Tris-buffered saline solution containing 5% dry milk. Hybridized bands were confirmed using an enhanced chemiluminescence (ECL) detection system (Describe the used ECL solution and measuring instrument information).

α-Tubulin (AbClon; AbC-2001) and NMDA receptor subunit NR1 (Life technologies; 32-0500) were used as the first antibodies and a peroxidase-conjugated second antibody (Jackson ImmunoResearch Laboratories) was used.

Data quantitative analysis was normalized to control group (control culture) using NIH ImageJ software and the expression ratios of total protein and biotin labeled proteins were compared.

As a result, as shown in FIG. 7a, it was confirmed that the expression ratio of NR1 protein was significantly decreased ($P<0.05$, n=3) on neuronal cell surface by miR-204, on the other hand, it was confirmed that the expression ratio of NR1 protein was significantly increased ($P<0.05$, n=3) by the miR-204 inhibitor.

In addition, to confirm whether the aging affects the protein expression of the NMDA receptor NR1 subunit, western blotting was performed in the same manner as above using the protein sample of Example 3-2.

As a result, as shown in FIG. 7b, as a result of confirming the expression of the NMDA receptor NR1 subunit from the young (of 2 months mouse) and the old (of months mouse) hippocampal tissues, It was confirmed that the expression of total NR1 protein was decreased by about 50% in the aging process. The above means that the expression of neurons' cell surface and total NR1 protein was decreased as the expression of EphB2 in neurons is decreased by miR-204, Having described specific portions of the present disclosure in detail, it will be apparent to a person having ordinary skills in the art that this specific description is merely a preferred embodiment and that the scope of the disclosure is not limited thereby. It is therefore intended that the scope of the disclosure be defined by the claims appended hereto and their equivalents.

What is claimed is:

1. A method of inhibiting a decrease in function in the hippocampus of a patient, comprising:
   (a) analyzing an expression of a miR-204-5p in a hippocampal tissue collected from the patient; and
   (b) determining that the hippocampus function is decreased when the expression of the miR-204-5p from the patient is increased and the expression of N-methyl-D-aspartate receptor (NMDA receptor) on a surface of a hippocampal nerve of the hippocampal tissue is decreased compared to the expressions of a control sample collected from a normal patient; and
   (c) administering to the hippocampus of the patient a nucleotide sequence that is complementary to miR-204-5p.

2. A method of inhibiting a decrease in function in the hippocampus of a patient, comprising:
   (a) analyzing an expression of a miR-204-5p in a hippocampal tissue collected from the patient; and
   (b) determining that the hippocampus function is decreased when the expression of the miR-204-5p from the patient is increased and the expression of N-methyl-D-aspartate receptor (NMDA receptor) on a surface of a hippocampal nerve of the hippocampal tissue is decreased compared to the expressions of a control sample collected from a normal patient; and
   (c) administering to the hippocampus of the patient a nucleotide sequence that is complementary to miR-204-5p,
   wherein, if the expression of the miR-204-5p is increased in step (b), an expression of a EphB2 protein is decreased, and resulting in a decrease in an expression of a NMDA receptor in the hippocampal nerves.

3. A method of inhibiting a decrease in function in the hippocampus of a patient, comprising:
   (a) analyzing an expression of a miR-204-5p in a hippocampal tissue collected from the patient; and
   (b) determining that the hippocampus function is decreased when the expression of the miR-204-5p from the patient is increased and the expression of N-methyl-D-aspartate receptor (NMDA receptor) on a surface of a hippocampal nerve of the hippocampal tissue is decreased compared to the expressions of a control sample collected from a normal patient; and
   (c) administering to the hippocampus of the patient a nucleotide sequence that is complementary to miR-204-5p,
   wherein if the expression of miR-204-5p is increased in step (b), an expression of a NR1 subunit, which is one of the NMDA receptor, is decreased.

* * * * *

SEQUENCE LISTING

<160> NUMBER OF SEQ ID NOS: 65

<210> SEQ ID NO 1
<211> LENGTH: 22
<212> TYPE: RNA
<213> ORGANISM: Artificial
<220> FEATURE:
<223> OTHER INFORMATION: miR-204-5p

<400> SEQUENCE: 1
uucccuuugu cauccuaugc cu                                              22

<210> SEQ ID NO 2
<211> LENGTH: 18
<212> TYPE: DNA
<213> ORGANISM: Artificial
<220> FEATURE:
<223> OTHER INFORMATION: EphB2-3'UTR-WT

<400> SEQUENCE: 2
aggattctca taagggaa                                                   18

<210> SEQ ID NO 3
<211> LENGTH: 18
<212> TYPE: DNA
<213> ORGANISM: Artificial
<220> FEATURE:
<223> OTHER INFORMATION: EphB2-3'UTR-MT

<400> SEQUENCE: 3
aggattctca tggagaga                                                   18

<210> SEQ ID NO 4
<211> LENGTH: 22
<212> TYPE: RNA
<213> ORGANISM: Artificial
<220> FEATURE:
<223> OTHER INFORMATION: miR-204-5p_2

<400> SEQUENCE: 4
aggcauagga ugacaaaggg aa                                              22

<210> SEQ ID NO 5
<211> LENGTH: 23
<212> TYPE: RNA
<213> ORGANISM: Artificial
<220> FEATURE:
<223> OTHER INFORMATION: mmu-miR-191-5p

<400> SEQUENCE: 5
caacggaauc ccaaaagcag cug                                             23

<210> SEQ ID NO 6
<211> LENGTH: 23
<212> TYPE: RNA
<213> ORGANISM: Artificial
<220> FEATURE:
<223> OTHER INFORMATION: mmu-miR-342-3p

<400> SEQUENCE: 6
ucucacacag aaaucgcacc cgu                                             23

<210> SEQ ID NO 7
<211> LENGTH: 22
<212> TYPE: RNA
<213> ORGANISM: Artificial

```
<220> FEATURE:
<223> OTHER INFORMATION: mmu-miR-99b-5p

<400> SEQUENCE: 7
cacccguaga accgaccuug cg                                              22

<210> SEQ ID NO 8
<211> LENGTH: 22
<212> TYPE: RNA
<213> ORGANISM: Artificial
<220> FEATURE:
<223> OTHER INFORMATION: mmu-miR-139-5p

<400> SEQUENCE: 8
ucuacagugc acgugucucc ag                                              22

<210> SEQ ID NO 9
<211> LENGTH: 22
<212> TYPE: RNA
<213> ORGANISM: Artificial
<220> FEATURE:
<223> OTHER INFORMATION: mmu-miR-433-3p

<400> SEQUENCE: 9
aucaugaugg gcuccucggu gu                                              22

<210> SEQ ID NO 10
<211> LENGTH: 22
<212> TYPE: RNA
<213> ORGANISM: Artificial
<220> FEATURE:
<223> OTHER INFORMATION: mmu-miR-1839-5p

<400> SEQUENCE: 10
aagguagaua gaacaggucu ug                                              22

<210> SEQ ID NO 11
<211> LENGTH: 23
<212> TYPE: RNA
<213> ORGANISM: Artificial
<220> FEATURE:
<223> OTHER INFORMATION: mmu-miR-144-5p

<400> SEQUENCE: 11
ggauaucauc auauacugua agu                                             23

<210> SEQ ID NO 12
<211> LENGTH: 22
<212> TYPE: RNA
<213> ORGANISM: Artificial
<220> FEATURE:
<223> OTHER INFORMATION: mmu-miR-125b-1-3p

<400> SEQUENCE: 12
acggguuagg cucuugggag cu                                              22

<210> SEQ ID NO 13
<211> LENGTH: 22
<212> TYPE: RNA
<213> ORGANISM: Artificial
<220> FEATURE:
<223> OTHER INFORMATION: mmu-miR-125b-2-3p

<400> SEQUENCE: 13
acaagucagg uucuugggac cu                                              22
```

```
<210> SEQ ID NO 14
<211> LENGTH: 23
<212> TYPE: RNA
<213> ORGANISM: Artificial
<220> FEATURE:
<223> OTHER INFORMATION: mmu-miR-298-5p

<400> SEQUENCE: 14
ggcagaggag ggcuguucuu ccc                                          23

<210> SEQ ID NO 15
<211> LENGTH: 21
<212> TYPE: RNA
<213> ORGANISM: Artificial
<220> FEATURE:
<223> OTHER INFORMATION: mmu-miR-411-5p

<400> SEQUENCE: 15
uaguagaccg uauagcguac g                                            21

<210> SEQ ID NO 16
<211> LENGTH: 16
<212> TYPE: DNA
<213> ORGANISM: Artificial
<220> FEATURE:
<223> OTHER INFORMATION: universal miRNA

<400> SEQUENCE: 16
gtgcagggtc cgaggt                                                  16

<210> SEQ ID NO 17
<211> LENGTH: 23
<212> TYPE: DNA
<213> ORGANISM: Artificial
<220> FEATURE:
<223> OTHER INFORMATION: EphA1-F

<400> SEQUENCE: 17
aggaagtcac tctaatggac aca                                          23

<210> SEQ ID NO 18
<211> LENGTH: 20
<212> TYPE: DNA
<213> ORGANISM: Artificial
<220> FEATURE:
<223> OTHER INFORMATION: EphA1-R

<400> SEQUENCE: 18
cctcactcca cccagtctct                                              20

<210> SEQ ID NO 19
<211> LENGTH: 21
<212> TYPE: DNA
<213> ORGANISM: Artificial
<220> FEATURE:
<223> OTHER INFORMATION: EphA2-F

<400> SEQUENCE: 19
gcacagggaa aggaagttgt t                                            21

<210> SEQ ID NO 20
<211> LENGTH: 22
<212> TYPE: DNA
<213> ORGANISM: Artificial
<220> FEATURE:
<223> OTHER INFORMATION: EphA2-R
```

<400> SEQUENCE: 20
catgtagata ggcatgtcgt cc                                    22

<210> SEQ ID NO 21
<211> LENGTH: 21
<212> TYPE: DNA
<213> ORGANISM: Artificial
<220> FEATURE:
<223> OTHER INFORMATION: EphA3-F

<400> SEQUENCE: 21
catgggtggg aagagatcag t                                     21

<210> SEQ ID NO 22
<211> LENGTH: 21
<212> TYPE: DNA
<213> ORGANISM: Artificial
<220> FEATURE:
<223> OTHER INFORMATION: EphA3-R

<400> SEQUENCE: 22
gatgctctcg gaatttgacg c                                     21

<210> SEQ ID NO 23
<211> LENGTH: 20
<212> TYPE: DNA
<213> ORGANISM: Artificial
<220> FEATURE:
<223> OTHER INFORMATION: EphA4-F

<400> SEQUENCE: 23
tggaatttgc gacgctgtca                                       20

<210> SEQ ID NO 24
<211> LENGTH: 20
<212> TYPE: DNA
<213> ORGANISM: Artificial
<220> FEATURE:
<223> OTHER INFORMATION: EphA4-R

<400> SEQUENCE: 24
cacttcctcc caccctcctt                                       20

<210> SEQ ID NO 25
<211> LENGTH: 20
<212> TYPE: DNA
<213> ORGANISM: Artificial
<220> FEATURE:
<223> OTHER INFORMATION: EphB1-F

<400> SEQUENCE: 25
cctcctccta tggactgccc                                       20

<210> SEQ ID NO 26
<211> LENGTH: 21
<212> TYPE: DNA
<213> ORGANISM: Artificial
<220> FEATURE:
<223> OTHER INFORMATION: EphB1-R

<400> SEQUENCE: 26
aaggccgtga agtctgggat a                                     21

<210> SEQ ID NO 27

```
<211> LENGTH: 19
<212> TYPE: DNA
<213> ORGANISM: Artificial
<220> FEATURE:
<223> OTHER INFORMATION: EphB2-F

<400> SEQUENCE: 27
gcggctacga cgagaacat                                                19

<210> SEQ ID NO 28
<211> LENGTH: 22
<212> TYPE: DNA
<213> ORGANISM: Artificial
<220> FEATURE:
<223> OTHER INFORMATION: EphB2-R

<400> SEQUENCE: 28
ggctaagtca aaatcagcct ca                                            22

<210> SEQ ID NO 29
<211> LENGTH: 21
<212> TYPE: DNA
<213> ORGANISM: Artificial
<220> FEATURE:
<223> OTHER INFORMATION: EphB3-F

<400> SEQUENCE: 29
catggacacg aaatgggtga c                                             21

<210> SEQ ID NO 30
<211> LENGTH: 22
<212> TYPE: DNA
<213> ORGANISM: Artificial
<220> FEATURE:
<223> OTHER INFORMATION: EphB3-R

<400> SEQUENCE: 30
gcggatagga ttcatggctt ca                                            22

<210> SEQ ID NO 31
<211> LENGTH: 22
<212> TYPE: DNA
<213> ORGANISM: Artificial
<220> FEATURE:
<223> OTHER INFORMATION: EphrinA1-F

<400> SEQUENCE: 31
cttcacgcct tttatcttgg gc                                            22

<210> SEQ ID NO 32
<211> LENGTH: 23
<212> TYPE: DNA
<213> ORGANISM: Artificial
<220> FEATURE:
<223> OTHER INFORMATION: EphrinA1-R

<400> SEQUENCE: 32
tggggattat gagtgatttt gcc                                           23

<210> SEQ ID NO 33
<211> LENGTH: 21
<212> TYPE: DNA
<213> ORGANISM: Artificial
<220> FEATURE:
<223> OTHER INFORMATION: EphrinA2-F

<400> SEQUENCE: 33
```
cgatacgcag tctactggaa c                                              21

<210> SEQ ID NO 34
<211> LENGTH: 21
<212> TYPE: DNA
<213> ORGANISM: Artificial
<220> FEATURE:
<223> OTHER INFORMATION: EphrinA2-R

<400> SEQUENCE: 34
ggtagtcgtt gatgctcacc t                                              21

<210> SEQ ID NO 35
<211> LENGTH: 19
<212> TYPE: DNA
<213> ORGANISM: Artificial
<220> FEATURE:
<223> OTHER INFORMATION: EphrinA3-F

<400> SEQUENCE: 35
cgtgcaggtg aacgtgaac                                                 19

<210> SEQ ID NO 36
<211> LENGTH: 21
<212> TYPE: DNA
<213> ORGANISM: Artificial
<220> FEATURE:
<223> OTHER INFORMATION: EphrinA3-R

<400> SEQUENCE: 36
gtaacgctgg aacttctcgg a                                              21

<210> SEQ ID NO 37
<211> LENGTH: 19
<212> TYPE: DNA
<213> ORGANISM: Artificial
<220> FEATURE:
<223> OTHER INFORMATION: EphrinB1-F

<400> SEQUENCE: 37
tgtggctatg gtcgtgctg                                                 19

<210> SEQ ID NO 38
<211> LENGTH: 20
<212> TYPE: DNA
<213> ORGANISM: Artificial
<220> FEATURE:
<223> OTHER INFORMATION: EphrinB1-R

<400> SEQUENCE: 38 ccaagcccctt cccacttagg                                               20

<210> SEQ ID NO 39
<211> LENGTH: 23
<212> TYPE: DNA
<213> ORGANISM: Artificial
<220> FEATURE:
<223> OTHER INFORMATION: EphrinB2-F

<400> SEQUENCE: 39
attatttgcc ccaaagtgga ctc                                            23

<210> SEQ ID NO 40
<211> LENGTH: 20
<212> TYPE: DNA

```
<213> ORGANISM: Artificial
<220> FEATURE:
<223> OTHER INFORMATION: EphrinB2-R

<400> SEQUENCE: 40
gcagcggggt attctccttc                                               20

<210> SEQ ID NO 41
<211> LENGTH: 20
<212> TYPE: DNA
<213> ORGANISM: Artificial
<220> FEATURE:
<223> OTHER INFORMATION: EphrinB3-F

<400> SEQUENCE: 41
tgctgctgtt aggttttgcg                                               20

<210> SEQ ID NO 42
<211> LENGTH: 22
<212> TYPE: DNA
<213> ORGANISM: Artificial
<220> FEATURE:
<223> OTHER INFORMATION: EphrinB3-R

<400> SEQUENCE: 42
ctgaggataa agcacgtaac cg                                            22

<210> SEQ ID NO 43
<211> LENGTH: 20
<212> TYPE: DNA
<213> ORGANISM: Artificial
<220> FEATURE:
<223> OTHER INFORMATION: Rgs3-F

<400> SEQUENCE: 43
agtgcaggat gcaggtcaac                                               20

<210> SEQ ID NO 44
<211> LENGTH: 22
<212> TYPE: DNA
<213> ORGANISM: Artificial
<220> FEATURE:
<223> OTHER INFORMATION: Rgs3-R

<400> SEQUENCE: 44
gaaagaagaa gtgctcgtgg aa                                            22

<210> SEQ ID NO 45
<211> LENGTH: 22
<212> TYPE: DNA
<213> ORGANISM: Artificial
<220> FEATURE:
<223> OTHER INFORMATION: RhoA-R

<400> SEQUENCE: 45
agcttgtggt aagacatgct tg                                            22

<210> SEQ ID NO 46
<211> LENGTH: 23
<212> TYPE: DNA
<213> ORGANISM: Artificial
<220> FEATURE:
<223> OTHER INFORMATION: RhoA-R

<400> SEQUENCE: 46
gtgtcccata aagccaactc tac                                           23
```

<210> SEQ ID NO 47
<211> LENGTH: 22
<212> TYPE: DNA
<213> ORGANISM: Artificial
<220> FEATURE:
<223> OTHER INFORMATION: Rock2-F

<400> SEQUENCE: 47
ttggttcgtc ataaggcatc ac                                              22

<210> SEQ ID NO 48
<211> LENGTH: 23
<212> TYPE: DNA
<213> ORGANISM: Artificial
<220> FEATURE:
<223> OTHER INFORMATION: Rock2-R

<400> SEQUENCE: 48
tgttggcaaa ggccataata tct                                             23

<210> SEQ ID NO 49
<211> LENGTH: 23
<212> TYPE: DNA
<213> ORGANISM: Artificial
<220> FEATURE:
<223> OTHER INFORMATION: cdk5-F

<400> SEQUENCE: 49
ccctgagatt gtgaagtcat tcc                                             23

<210> SEQ ID NO 50
<211> LENGTH: 22
<212> TYPE: DNA
<213> ORGANISM: Artificial
<220> FEATURE:
<223> OTHER INFORMATION: cdk5-R

<400> SEQUENCE: 50
ccaatttcaa ctccccattc ct                                              22

<210> SEQ ID NO 51
<211> LENGTH: 21
<212> TYPE: DNA
<213> ORGANISM: Artificial
<220> FEATURE:
<223> OTHER INFORMATION: Mapk1-F

<400> SEQUENCE: 51
ggttgttccc aaatgctgac t                                               21

<210> SEQ ID NO 52
<211> LENGTH: 23
<212> TYPE: DNA
<213> ORGANISM: Artificial
<220> FEATURE:
<223> OTHER INFORMATION: Mapk1-R

<400> SEQUENCE: 52
caacttcaat cctcttgtga ggg                                             23

<210> SEQ ID NO 53
<211> LENGTH: 23
<212> TYPE: DNA
<213> ORGANISM: Artificial
<220> FEATURE:

<223> OTHER INFORMATION: Rasa1-F

<400> SEQUENCE: 53
tgtggtgatt actacattgg tgg                                           23

<210> SEQ ID NO 54
<211> LENGTH: 23
<212> TYPE: DNA
<213> ORGANISM: Artificial
<220> FEATURE:
<223> OTHER INFORMATION: Rasa1-R

<400> SEQUENCE: 54
cgccttctat cttctactgg ctc                                           23

<210> SEQ ID NO 55
<211> LENGTH: 22
<212> TYPE: DNA
<213> ORGANISM: Artificial
<220> FEATURE:
<223> OTHER INFORMATION: Pak2-F

<400> SEQUENCE: 55
aacggagagc tagaagacaa gc                                            22

<210> SEQ ID NO 56
<211> LENGTH: 21
<212> TYPE: DNA
<213> ORGANISM: Artificial
<220> FEATURE:
<223> OTHER INFORMATION: Pak2-R

<400> SEQUENCE: 56
tggaacagaa ggcaaaggtt t                                             21

<210> SEQ ID NO 57
<211> LENGTH: 21
<212> TYPE: DNA
<213> ORGANISM: Artificial
<220> FEATURE:
<223> OTHER INFORMATION: Fyn-F

<400> SEQUENCE: 57
acctccatcc cgaactacaa c                                             21

<210> SEQ ID NO 58
<211> LENGTH: 20
<212> TYPE: DNA
<213> ORGANISM: Artificial
<220> FEATURE:
<223> OTHER INFORMATION: Fyn-R

<400> SEQUENCE: 58
cgccacaaac agtgtcactc                                               20

<210> SEQ ID NO 59
<211> LENGTH: 23
<212> TYPE: DNA
<213> ORGANISM: Artificial
<220> FEATURE:
<223> OTHER INFORMATION: Met-F

<400> SEQUENCE: 59
gtgaacatga agtatcagct ccc                                           23

<210> SEQ ID NO 60
<211> LENGTH: 21
<212> TYPE: DNA
<213> ORGANISM: Artificial
<220> FEATURE:
<223> OTHER INFORMATION: Met-R

<400> SEQUENCE: 60
tgtagtttgt ggctccgaga t                                              21

<210> SEQ ID NO 61
<211> LENGTH: 20
<212> TYPE: DNA
<213> ORGANISM: Artificial
<220> FEATURE:
<223> OTHER INFORMATION: Actin-F

<400> SEQUENCE: 61
ggctgtattc ccctccatcg                                                20

<210> SEQ ID NO 62
<211> LENGTH: 22
<212> TYPE: DNA
<213> ORGANISM: Artificial
<220> FEATURE:
<223> OTHER INFORMATION: Actin-R

<400> SEQUENCE: 62
ccagttggta acaatgccat gt                                             22

<210> SEQ ID NO 63
<211> LENGTH: 18
<212> TYPE: DNA
<213> ORGANISM: Artificial
<220> FEATURE:
<223> OTHER INFORMATION: miR-204-5p

<400> SEQUENCE: 63
ttccctttgt catcctat                                                  18

<210> SEQ ID NO 64
<211> LENGTH: 21
<212> TYPE: RNA
<213> ORGANISM: Artificial
<220> FEATURE:
<223> OTHER INFORMATION: scramble mimic

<400> SEQUENCE: 64
gguucguacg uacacuguuc a                                              21

<210> SEQ ID NO 65
<211> LENGTH: 22
<212> TYPE: RNA
<213> ORGANISM: Artificial
<220> FEATURE:
<223> OTHER INFORMATION: miR-204 inhibitors

<400> SEQUENCE: 65
aggcauagga ugacaaaggg aa                                             22